United States Patent [19]

Larsen et al.

[11] 4,240,027
[45] Dec. 16, 1980

[54] ELECTROMAGNETIC METHOD FOR THE NONINVASIVE ANALYSIS OF CELL MEMBRANE PHYSIOLOGY AND PHARMACOLOGY

[75] Inventors: Lawrence E. Larsen, Silver Spring; John H. Jacobi, Bowie, both of Md.

[73] Assignee: The United States of America as represented by the Secretary of the Army, Washington, D.C.

[21] Appl. No.: 938,625

[22] Filed: Aug. 31, 1978

[51] Int. Cl.³ .......................................... G01R 27/26
[52] U.S. Cl. ................................ 324/57 R; 324/61 R
[58] Field of Search ................. 324/57 R, 60 R, 60 C, 324/61 R, 61 P; 128/734

[56] References Cited

PUBLICATIONS

Stibitz et al., "A computer-Aided . . . ", Medical and Biological Engineering, Jan. 1974, pp. 100–104.
Hyde, P. J., "Wide Frequency Range . . . ", Proc. of the IEE, vol. 117, No. 9, Sep. 1970, pp. 1891–1901.
Hewlett-Packard Catalog, 1970, pp. 386–388, Hewlett-Packard, Co., Palo Alto, Calif.

Primary Examiner—Ernest F. Karlsen
Attorney, Agent, or Firm—William G. Gapcynski; Sherman D. Winters; Werten F. W. Bellamy

[57] ABSTRACT

A method for electromagnetic analysis of cellular or cell ghost physiology and pharmacology without disrupting the physcial integrity of the cell membrane is described. The method utilizes the technique of multifrequency automatic network analysis and signal processing to derive complex permittivities from the error corrected complex reflection coefficient of cell containing samples at each measured frequency. Complex permittivity at each frequency is then related to the dispersion in dielectric conductivity (a term which includes ohmic and non-ohmic losses) thereby measuring the ion permeability barrier and transport functions of the cell membrane and ion distribution inside of and outside of the cell membrane. The method measures the complex reflection coefficient of a capacitive termination containing a cellular sample as high frequencies are applied. Meaningful data can be developed in the range of frequencies of from 100 KHz to 100 MHz depending upon the exact nature of the cells and the automatic network analyzer used.

6 Claims, 22 Drawing Figures

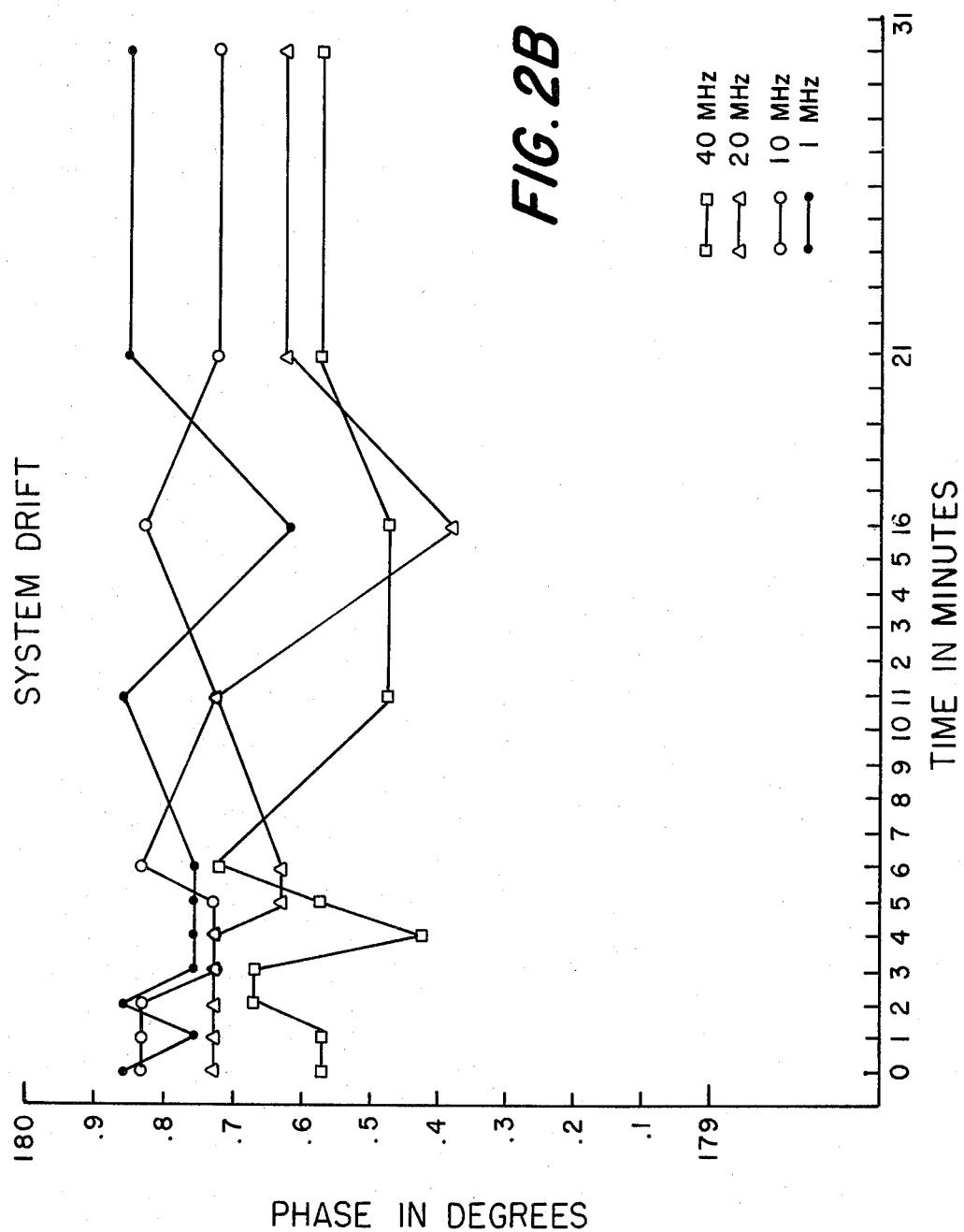

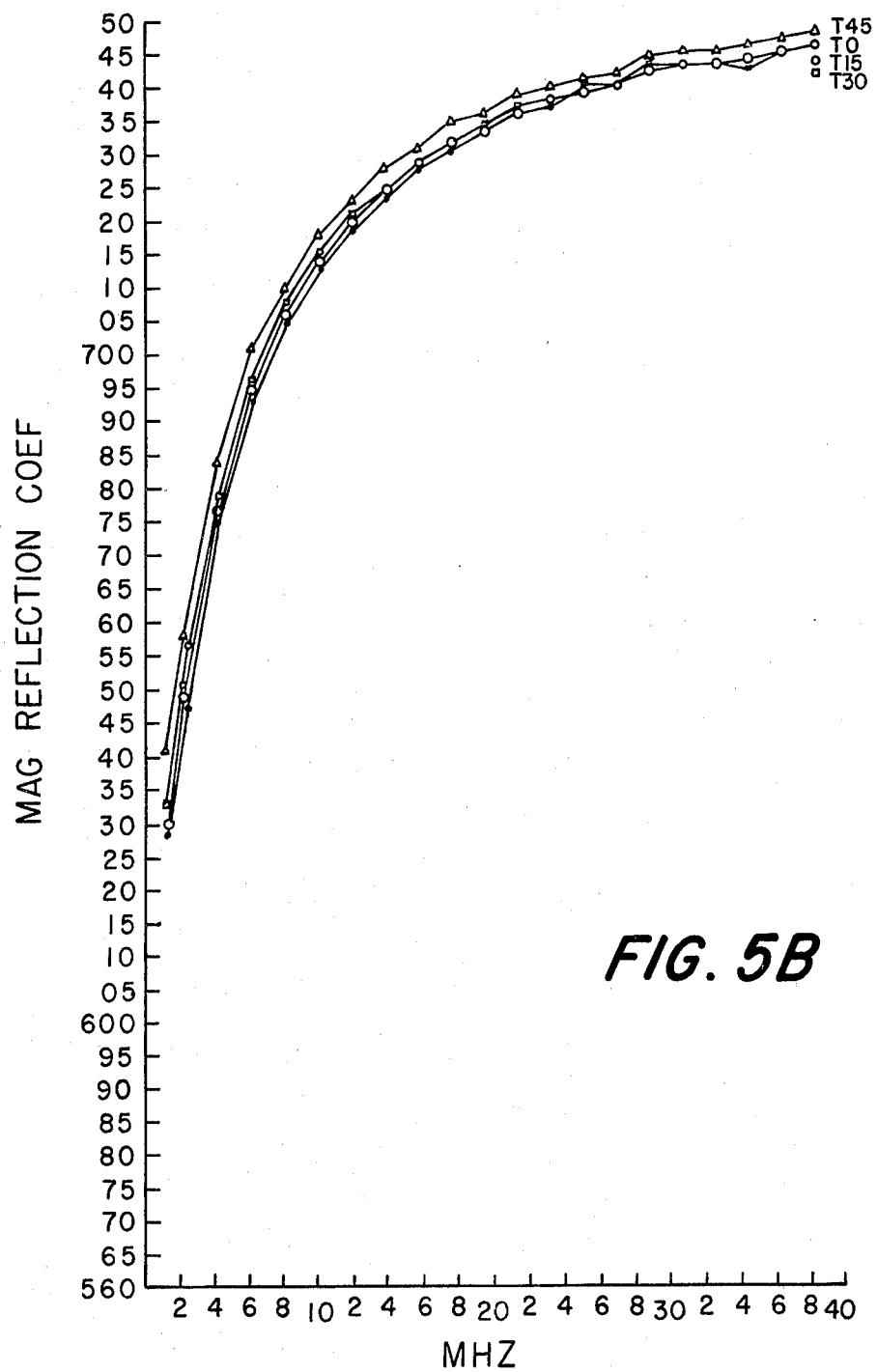
FIG. 5B — SHAKER CONTROL

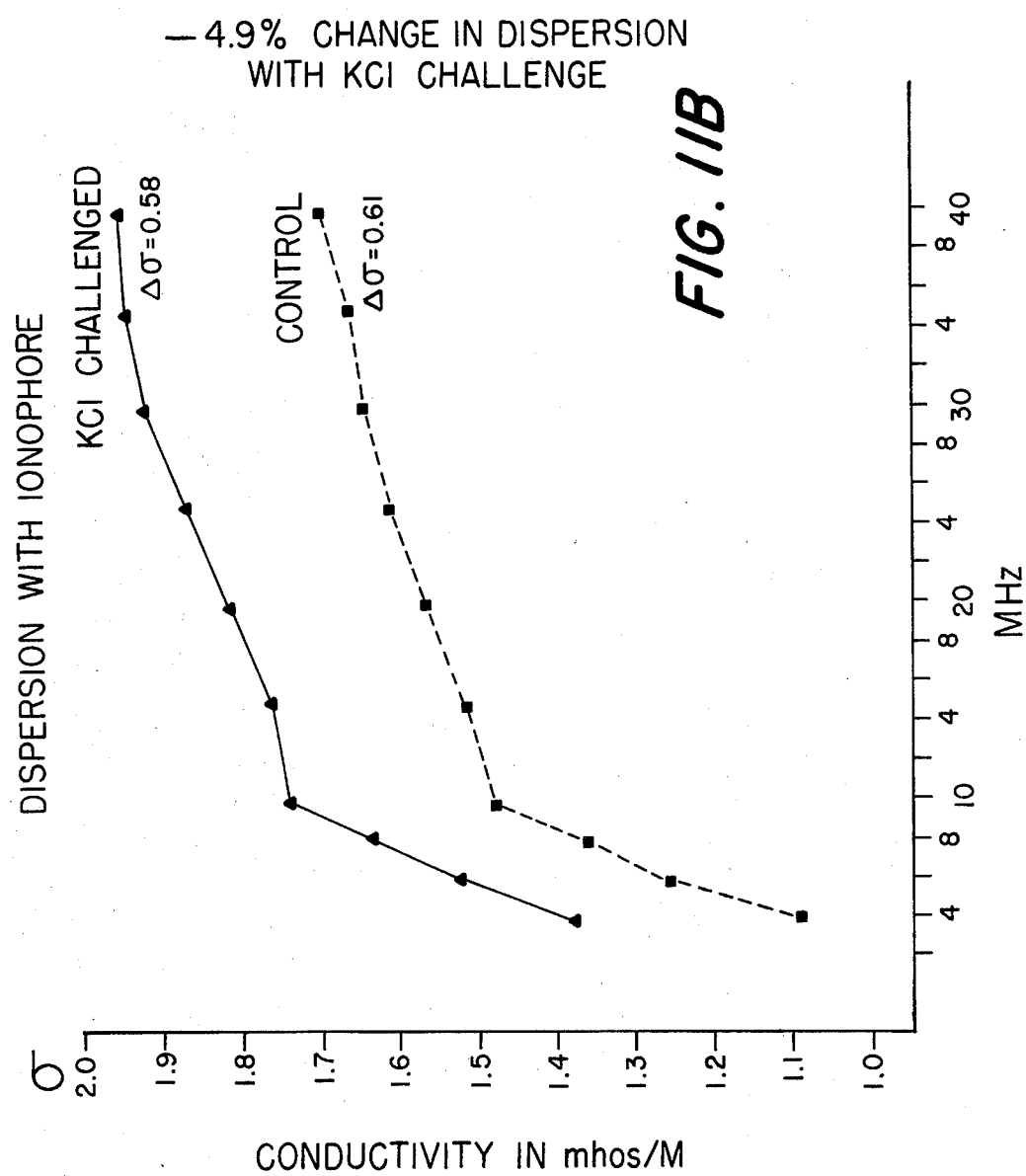

ELECTROMAGNETIC METHOD FOR THE NONINVASIVE ANALYSIS OF CELL MEMBRANE PHYSIOLOGY AND PHARMACOLOGY

This invention relates to the electromagnetic analysis of biological cell membrane functions and in particular to a noninvasive method for evaluating the ion permeability barrier functions of cell membrane. The method of this invention then provides an accurate means for evaluating the creation of specialized electrolytic and molecular environments within the cell by the cell membrane and its alteration, for example, by various drug actions.

Previous studies state that chemical destruction of the cell membrane ghosts is necessary before the dispersion is materially altered except at audio frequencies such as 15 KHz. These previous studies then did not anticipate meaningful change in dispersion at HF band frequencies. However, it has been discovered that the previous studies actually measured the dispersion of vesicles. Upon destroying the cell membrane by sonication, it has been discovered that dispersion in the high frequency band, as will be subsequently explained, should be measured in order to evaluate cell membrane functions, and that by using automatic network analysis and a lumped capacitance method, the complex permittivity and therefore the conductivity and dielectric constant can be rapidly and accurately measured at different selected frequencies in order to give a true picture of cell membrane functions without the destruction of cell membrane.

The biological analysis of membrane function began with invasive biochemical and physiological methods wherein the structural integrity of the cell membrane is compromised. The activity of the cell membrane was inferred by the comparison of ionic environments of the cell interior with those exterior to the cell membrane. Cells were separated from their suspending medium and the cell structure, especially the cell membrane, disrupted to exteriorize the intracellular contents for conventional quatitative and qualitative chemical analysis. Invasive methods may also directly instrument the intracellular space.

Noninvasive methods have made use of membrane bound intracellular fluorescent molecules. This technique was first used in the giant axon of marine invertebrates. Recently, this method has been applied to mammalian erythrocytes. However, in the case of these cells, direct measurement of the transmembrane potential is not possible due to their small diameter, and excessive artifact results when these cells are impaled with microelectrodes. In addition, fluorescent measurements applied to intact erythrocytes are usable only for short term comparative measurements of 30 to 90 seconds due to the practical limitation of existing fluorospectophotometers. Furthermore, these measurements must be done in very dilute suspensions of less than 0.5%. Accordingly, the evaluation by this method requires removal of the blood, and in situ measurements are impossible.

Another noninvasive method makes use of cell mobility in static electric fields. This technique obviously requires cells therefore in suspension and limits interpretability to cells which normally exist in suspension such as bacteria, blood cells, and the like. This procedure may not be applied to solid tissues wherein cells are interconnected.

More general noninvasive techniques for analyzing membrane physiology and pharmacology are known, and it is known to analyze the dielectric relaxation component with electromagnetic measurements in the 100 KHz to 100 MHz band. See Presman, *Electromagnetic Fields and Life*, Plenum, New York, pages 34–44, 1970. This dielectric relaxation is thought to result from two factors: (1) the frequency dependent electromagnetic properties of the cell membrane itself; and (2) the different complex permittivities which characterize the intracellular and extracellular spaces. The heterogeneous dielectric nature of cell systems is of utmost importance not only for the relaxation process, but because this condition is related to a fundamental biological property of cell systems, i.e., the creation of specialized electrolyte and molecular environments within the cell.

Dielectric relaxation is a dispersion phenomenon, and is explicitly a frequency dependent process. Relaxation processes are typically associated with the liquid state and in the classic formulation, relaxation consists of a simultaneous transition of the dielectric constant downward and upward transition of conductivity (an expression which includes both ohmic and non-ohmic losses). At the midpoint of this transition, the loss tangent peaks. Energy extraction from the field is maximized at the corresponding frequency. This frequency is known as the relaxation frequency of the process. See Debye, *Polar Molecules*, The Chemical Catalog, New York, 1929.

Heterogeneous dielectrics are also characterized by relaxation spectra. These spectra are described by the Maxwell-Wagner formulation wherein the contributing complex permittivites are volume weighted. See Fricke, "The Maxwell-Wagner Dispersion In A Suspension of Ellipsoids", *J. Phys. Chem.*, 57:934–937, 1953. While the form of the dispersion is the same as in the Debye case, the mechanism is different in that the interfacial polarization combines with electronic polarization.

In the 1930's, it became apparent that frequency dependent analysis of the complex admittance of intact red blood cells suspended in electrolyte solutions could serve an important role in the analysis of membrane function as a diffusion barrier. See Fricke and Curtis, "The Electric Impedance of Hemolyzed Suspension of Mammalian Erythrocytes", *J. Gen. Physiol.*, 18:821–836, 1935. The selective permeability of cell membranes then become associated with the process of active transport and the site of numerous pharmacological studies to elucidate the cellular basis for various drug functions.

The key element in evaluating various drug actions through the study of membrane biochemistry and physiology is the measurement of dispersion (frequency dependence) of the complex permittivity of the cell system. Information of this type may be presented in many forms. For example, lumped element equivalent circuits, complex plane plots of the admittance, complex plane plots of the permittivity, and complex plane plots of the scattering parameters have been utilized. In these instances, the locus of points traced out in the complex plane as frequency is varied provides useful information concerning the nature and number of relaxation processes contributing to any relaxation spectrum.

The method previously used are well documented in literature of dielectric or permittivity measurement. See for example Bussey, "Measurement of RF Properties of Materials: A Survey", *Proc. IEEE*, 55:1046–1053, 1967. Cell membrane dispersion measurements have extended from audio to microwave frequencies. The methods for such measurements vary from the impedance brdige with lumped circuit element substitution, to slotted line VSWR (Voltage Standing Wave Ratio) measurements and cavity perturbation techniques. These methods however are characterized by a comparatively slow rate of data acquisition and a relatively limited range of frequencies which could be studied with a single instrument. For example, waveguide systems are limited to about 20% band width due to the need to maintain constant modes. Further, waveguide methods are limited to frequencies in the microwave range due to the required physical size which is too large for use in the high frequency band where the dielectric relaxation takes place. Cavity perturbation methods are extremely narrow band and cannot make measurements over the 10 or 20 octaves that spectral characterization requires. This leaves transmission line methods as the only practical method. In the past, such measurements were made with extremely slow and laborious methods in such transmission lines. In impedance bridge and circuit element substitution techniques, the laborious manual methods require from 30 to 60 minutes to collect data on only two or three frequencies.

The result of utilizing these prior techniques has been a paucity of physiological and pharmacological application due to the large number of measurements which must be made within the constraints of many octaves of frequency at many discrete frequencies in the time course of many drug actions.

The physiological interpretation of cell membrane relaxation in the band of 1 to 100 MHz is based on the heterogeneous nature of the "bulk" dielectric and the capacitance of the cell membrane. See Schwan, "Electric Properties of Tissue and Cell Suspensions". *Advanc. Biol. Med. Phys.*, 5:147–209, 1957; and Schwan, "Molecular Response Characteristics to Ultra-High Frequency Fields". *Proc. Second Tri-Serv. Conf. on Biol. Effects on Microwave Energy*, (AD 131 477) pages 33–48, 1958.

At the low frequency limiting value, the reactance of the membrane is sufficient to attenuate current induction in the intracellular space; but at the upper frequency limiting value, the reactance is small compared to the membrane resistance. Under these conditions, appreciable currents are induced in the intracellular space. Since the intracellular space in a normal cell has a different complex permittivity than the extracellular space, the dispersion in conductivity represents the ion permeability barrier functions of the cell membrane. If the physical integrity of the cell membrane is disrupted, the conductivity of the intracellular space is mixed with that of the extracellular space and the dispersion in conductivity is reduced, or in the limiting case, removed.

The location in frequency for the cell membrane dispersion is dependent on the tissue type and its physiological or pathological state. The generally recognized location for dielectric relaxation of, for example, red cell suspensions in isotonic electrolyte media is in the 1 to 100 MHz band.

It has been discovered however that cell membrane characteristics may be accurately and reliably evaluated at high speed by the non-invasive technique of this invention. In particular, ion permeability and ion distribution within and outside the cell may be analyzed by measurement of the frequency dependent reflection coefficient with electromagnetic energy in the HF band. By using automatic network analysis, selective permeability may be accurately and quickly evaluated in cellular samples including both cell suspensions or tissue biopsies which have been slurried without destroying cell content.

Automatic network analysis is performed to measure the complex reflection coefficient of a capacitivie termination. The termination consists of a coaxial chamber utilizing a male center conductor and a shell-cap to form a compacitor into which samples and standards are introduced and evaluated over a range of frequencies. The reflection coefficient is measured in for example 1 MHz steps throughout a range of for example from 2 to 40 MHz and the measurements corrected for frequency dependent components proximal and distal to the test set by reference to a set of network standards. In the cell suspensions evaluated herein, it was not necessary to exceed frequencies of 40 MHz because the upper limiting value of the dispersion had been reached. However, in other cellular samples, higher values might be necessary. As will be subsequently explained, it is not anticipated that values exceeding 100 MHz would be necessary, and the calibration technique utilized for the preset instrument did not employ frequencies which exceed 200 MHz.

In general, frequencies above 100 KHz and less than the relaxation frequency measure the extracellular space dispersion. Frequencies above about 1 MHz measure both intracellular space dispersion and extracellular space dispersion, at the higher frequencies the reactance is small compared to the membrane resistance. At frequencies approaching the upper frequency limiting value, appreciable currents are induced in the intracellular space. Since the intracellular space in a normal cell (variations do exist for various specialized tissues) has a different complex permittivity than the extracellular space, the dispersion in conductivity represents the ion permeability barrier functions of the cell membrane. If the physical integrity of the cell membrane is disrupted, the media of the intracellular space are mixed with those of the extracellular space and the dispersion is reduced, or in the limiting case, when the cell membrane is sonicated, removed.

Accordingly, it is an object of this invention to provide a non-invasive technique for evaluating cell membrane permeability characteristics and total ion distribution inside and outside of the cell membrane.

It is the further object of this invention to evaluate cell membrane permeability characteristics by utilizing high speed automatic network analysis. It is a further object of this invention to accurately and reliably determine the complex reflection coefficient of a cellular sample stepwise over a frequency range from 2 to about 40 MHz by utilizing an automatic network analyzer for one port networks.

These and other objects will become readily apparent with reference to the drawings and following description wherein FIG. 1 is a cross-sectional view of the coaxial capacitance chamber used for HF band dispersion analysis;

FIG. 2 is a graph of the magnitude of the complex reflection coefficient displayed as a function of frequency for intact and for sonicated red blood cells (RBC) suspensions;

FIGS. 2A and 2B are graphs of the system drift as expressed as temperal variation in the magnitude, FIG. A, and the phase, FIG. B, of the reflection coefficient at four frequencies with isotonic saline in the test chamber;

FIGS. 5, 5A and 5B are graphs of the dispersion of the magnitude of the reflection coefficient for a rabbit erythrocyte in saline suspension (34% Hct) expressed as a function of time in minutes since the origin with oubain incubation in FIG. 5, with water incubation of equal volume in FIG. 5A, and with no treatment except periodic shaking in FIG. 5B;

Figure 10:
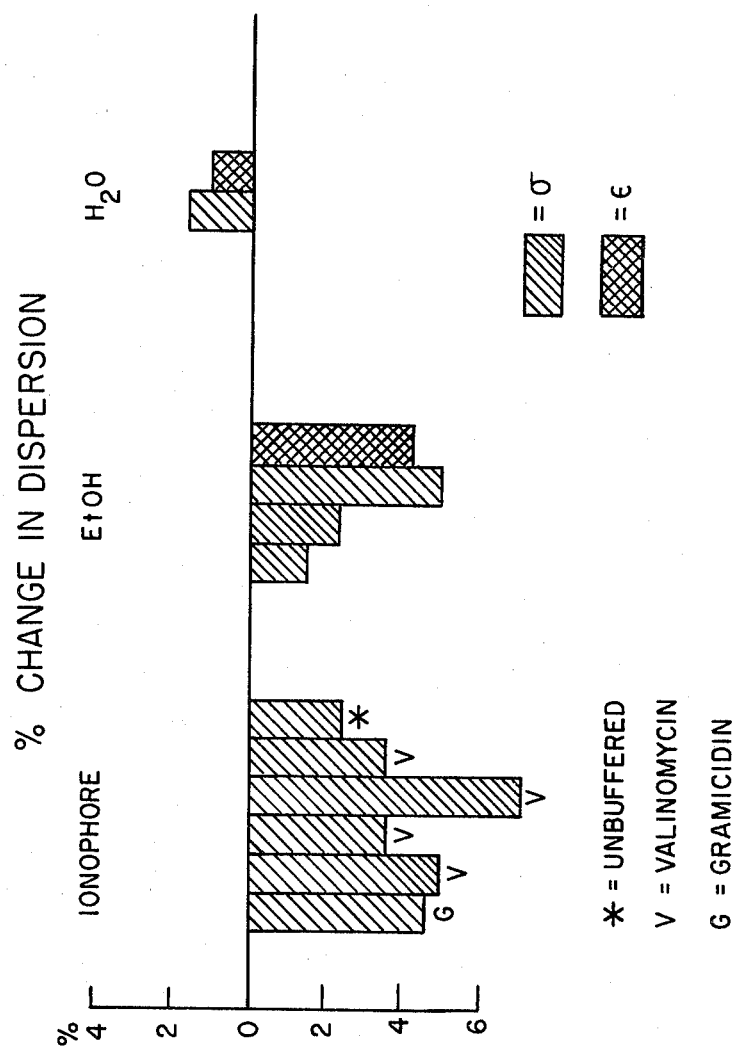
Figure 11:
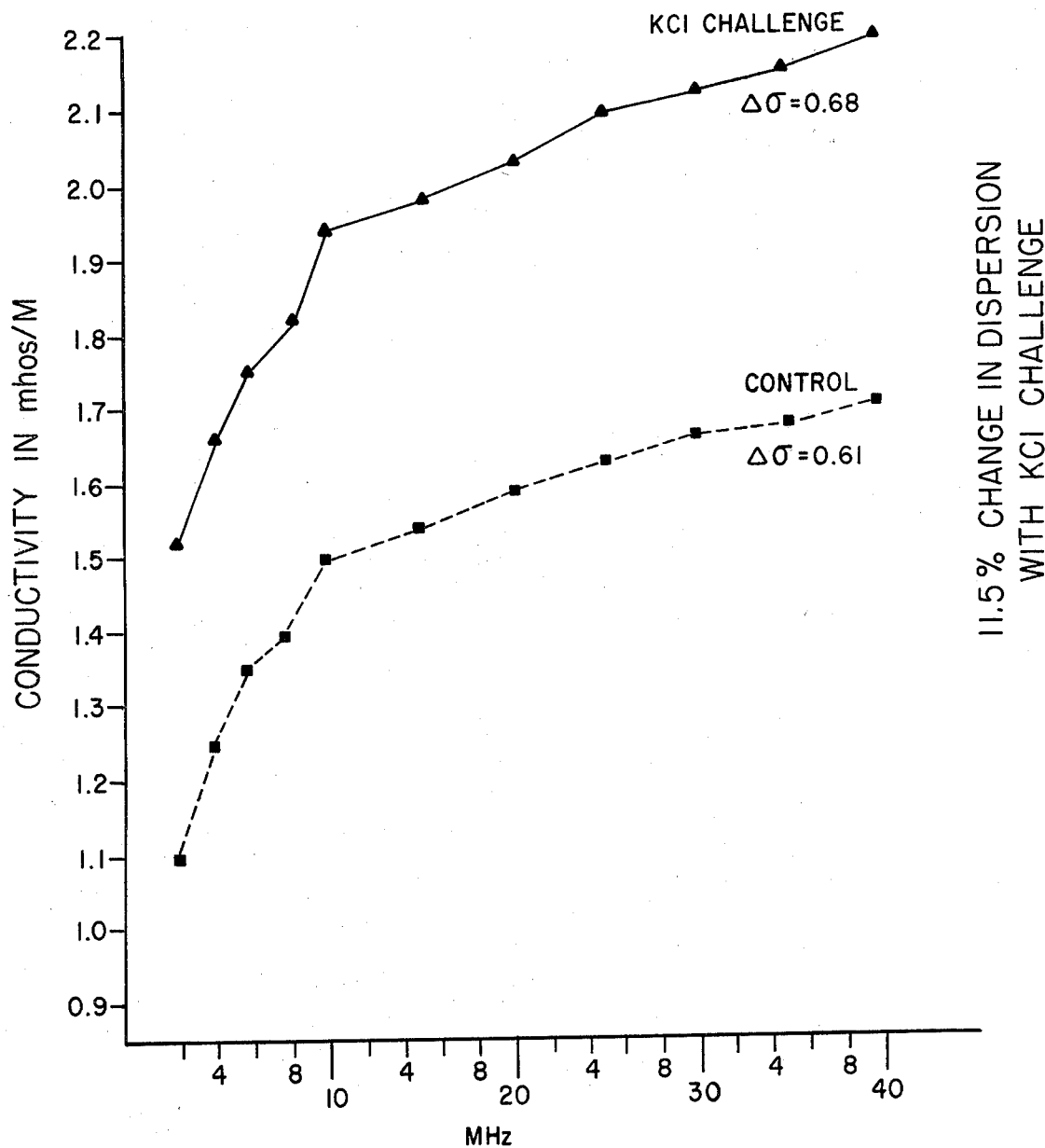
Figure 11A:
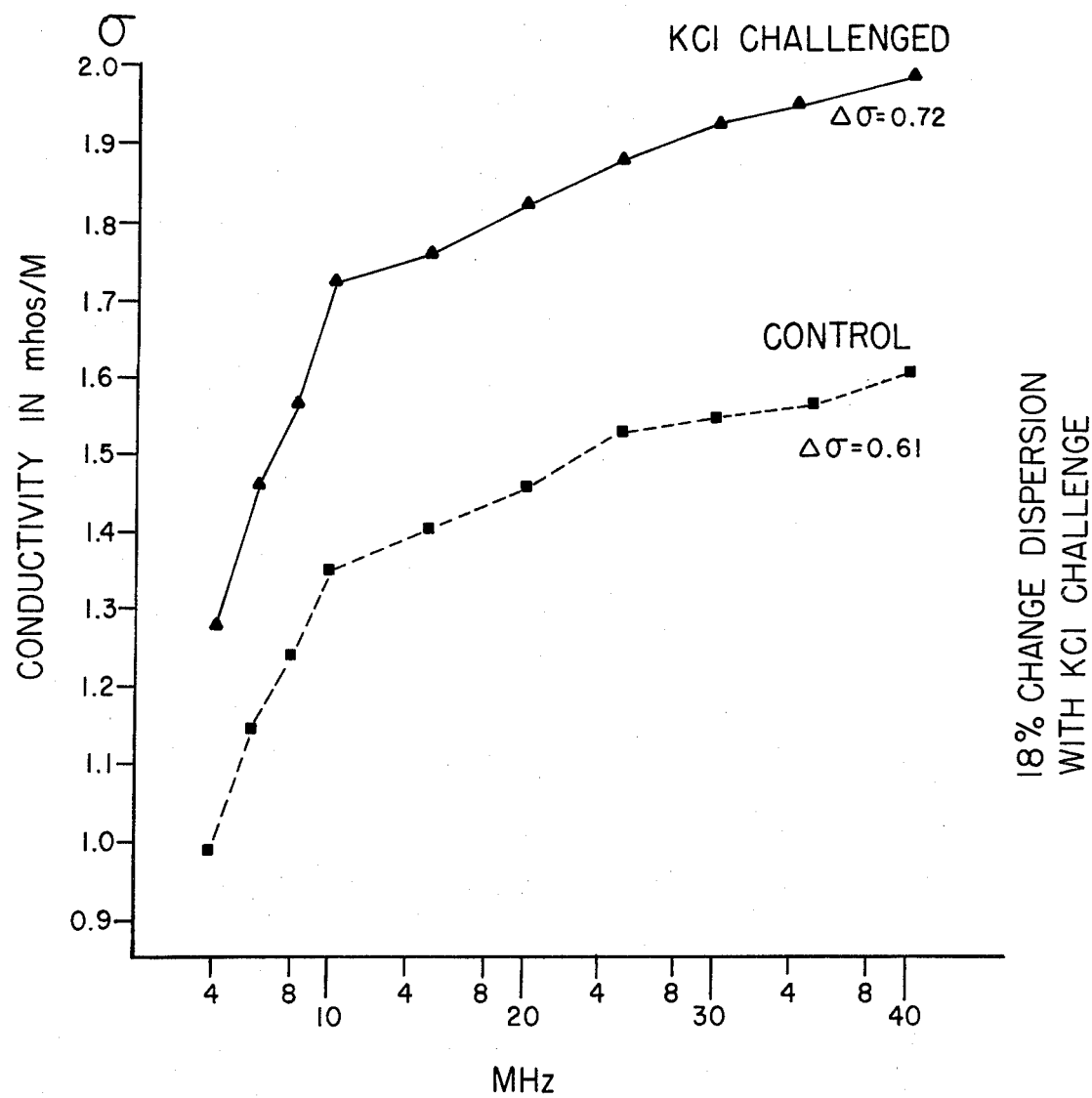
Figure 11C:
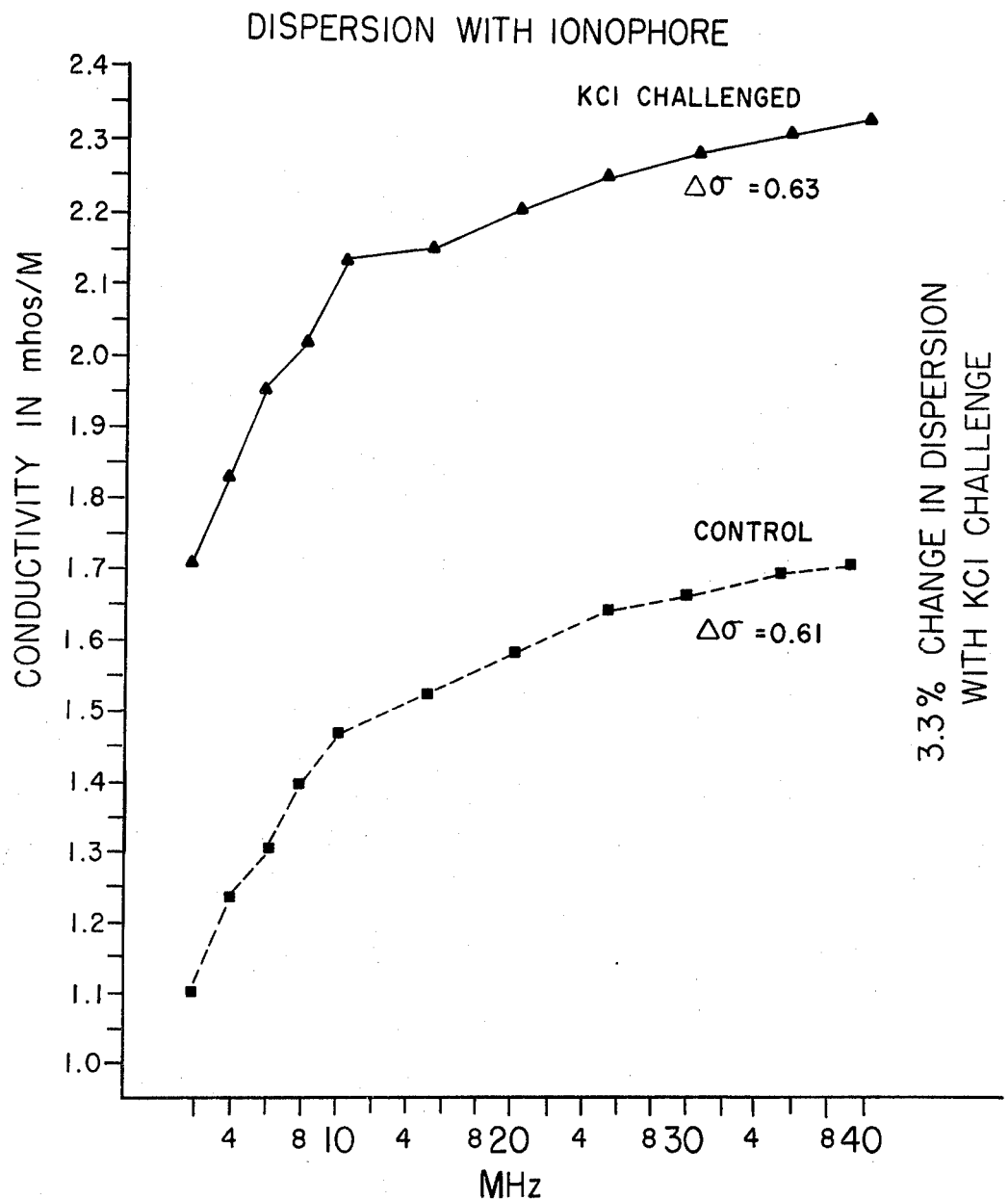

FIG. 10 is a graph of the effects of ionophore alone and ionophore solvents alone on the dispersion of complex permittivity in a rabbit erythrocyte suspension with and without buffers; and FIGS. 11, 11A, 11B and 11C are graphs of the effects of a hypertonic KCl challenge (30 μL of 3 MKCL) on a MOPS-TRIS buffered (pH 7.0) rabbit erythrocyte suspension; the dispersions in conductivity are presented for KCl challenge without in FIGS. 11 and 11A and with in FIGS. 11B and 11C prior treatment with ionophore.

This invention comprises the discovery that the ion permeability barrier/membrane integrity functions of cell membrane may be accurately evaluted at high speed for many discrete frequencies by automatic network analysis. As is well known to those skilled in the art, automatic network analysis involves transmitting a known signal input to a test environment with two ports and measuring the outputs therefrom. More accurately, the amplitude and phase of the output signal at either or both ports are recorded relative to an input signal, which may be applied to either port 1 or port 2, and in the present invention the automatic network analyzer is utilized to measure the magnitude and phase angle of the output of port 1 with signal applied to port 1 to calculate the reflection coefficient. The reflection coefficient may then be utilized to calculate the dielectric constant (E') and conductivity (σ) at measured frequencies according to the method of Jacobi, "A Lumped Capacitance Technique for Permittivity Measurements at VHF/UHF Frequencies", Proc. 1977 International Synposium IEEE APS/USNCURSI, October 1976, which articler is hereby incorporated by reference. The method is also described in U.S. patent application Ser. No. 938,570 entitled "Calibration Method for Lumped Capacitance Measurement of Complex Permittivity at HF, VHF and UHF Frequencies". John H. Jacobi et. al, inventors, filed on even date herewith. The disclosure of said application is hereby incorporated by reference. For purposes of illustration of the method of this invention, electromagnetic analysis on a variety of different cell suspensions was performed with an automatic network analyzer for one part network utilizing a Hewlett Packard Model 8507B Automatic Network Analyzer with the phase locked source option. Measurements were corrected for frequency dependent components proximal to and distal to the test set by reference to a set of network standards. The corrections were applied by means of a modified version of the Hewlett Packard program AIM (Accuracy Improvement Method) described in the 1978 Hewlett Packard Instruction Catalog. The description in said catalog is hereby incorporate by reference. All measurements included a DC block at the test port. The HP8507B measured the complex reflection coefficient of a capacitive termination on port 1 of a test set.

Figure 1:
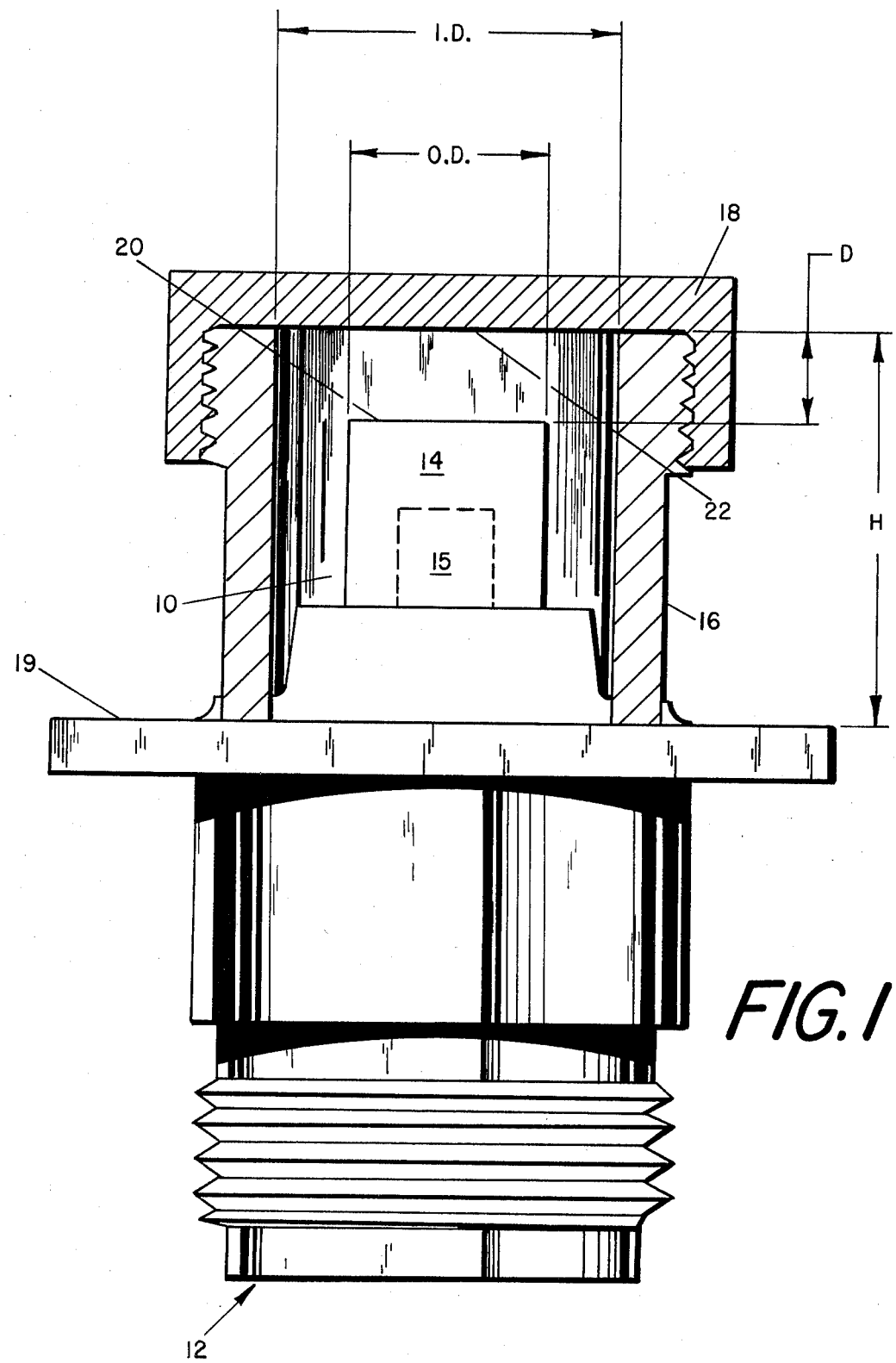

With reference to FIG. 1, the termination consisted of a coaxial chamber 10 fabricated from a type N bulkhead conductor 12; a center conductor 14 formed with a conductor shell 16 and cap 18. Blood samples or cell samples and dieletric standards were introduced into the capacitor chamber 10 for test purposes by the removal of cap 18 from shell 16. The cap was then replaced for test purposes. The dimensions were as follows: the Length H of shell 16 was 12.5 millimeters. The outside diameter (O.D.) of condcutor 14 was 6.35 millimeters and the inside diameter (I.D.) of shell 16 was 11.43 millimeters. The distance between the upper surface 20 of conductor 14 and the inner surface 20 of cap 18 when mounted on shell 16 was 2.54 millimeters. This latter distance is identified in FIG. 1 by the reference character D. The chamber 10 was calibrated for capacitance according to the method of Jacobi by measuring the reflection coefficient at each frequency for air and deionized water, as described in the aforementioned U.S. patent application. Measurements at 40 discrete frequencies were accomplished in 15 seconds in 1 MHz steps over a range of 1 to 40 MHz.

At frequencies in the lower range of the 8507B, the phase angles were obtained by analytical continuation and interpolation. This procedure was applied in such a way that very small corrections were obtained at frequencies above 4 or 5 MHz. At 3 MHz and below, the corrections were significant in that they amounted to as much as 0.8 degree. The corrected reflection coefficient data was processed according to the above methods of Jacobi to yield the relative dielectric constant and cnductivity at each measured frequency.

Calibration steps also included the use of platinum-platinum black electrode coating to evaluate polarization effects at the electrode-electrolyte interface. See Schwan, H. P., Physical Techniques in Biological Research, Vol. VI B, Chapter 6, Academic Press, New York, 1963. Other surface treatments tested were polished copper and bright platinum. Bright platinum electrodes were produced by platinum plating platinum (about 100 microinches) over the copper with an intermediate layer of Watts nickel (around 100 to 200 microniches) over the original copper surface. Platinum black was produced according to the well known method wherein 2% lead acetate is added to a platinum salt solution. The thickness of the platinum black over the platinum plate was determined by the tables in Jones and Bollinger, "Measurement of Conductivity of Electrolytes: VIII. On Platinization", *J. Am. Chem. Soc.* 57:281–284, 1936 (around 50–200 coulombs). The underlying platinum plating was roughened by etching in order to maximize surface area for greatest polarization capacitance and minimal polarization resistance. All plating solutions were obtained from the Electrometalics Division of Englehard Industries, Union, New Jersey.

The electrode interface was characterized by an equivalent polarization impedance in series with the sample impedance. That is, identical ionic conditions including cells, buffer, temperature and species were measured in both bright copper and platinum black chambers to establish a set of equivalents. Corrective factors were then generated to accommodate use of the polarizable system for selected later experiments.

Additional data was collected at both 26° C. and 37° C. with both rabbit and sheep blood in saline and MOPS-TRIS suspensions in the platinum/platinum black chamber in order to assist comparability to other studies.

Figure 2:
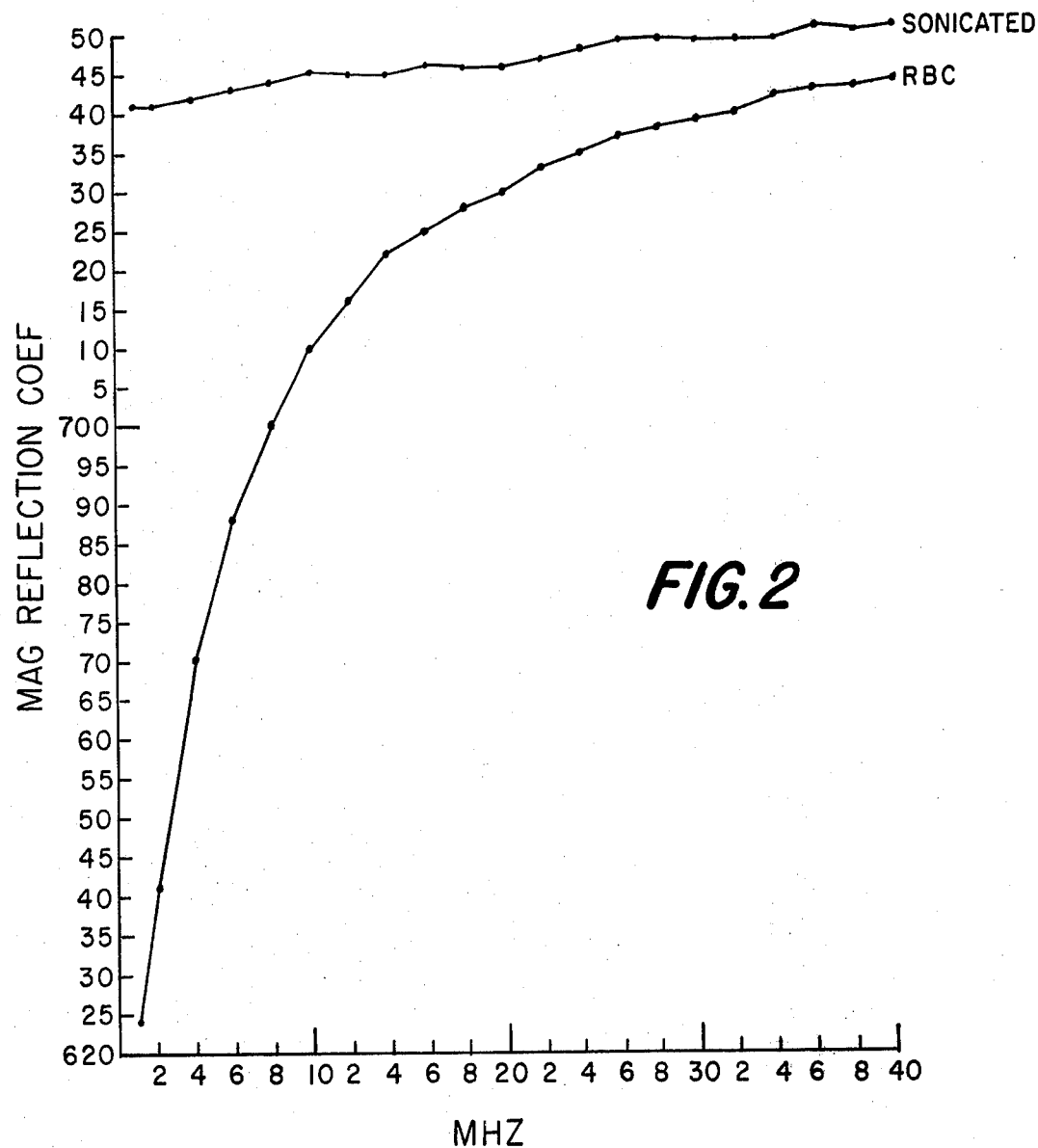
Figure 2A:
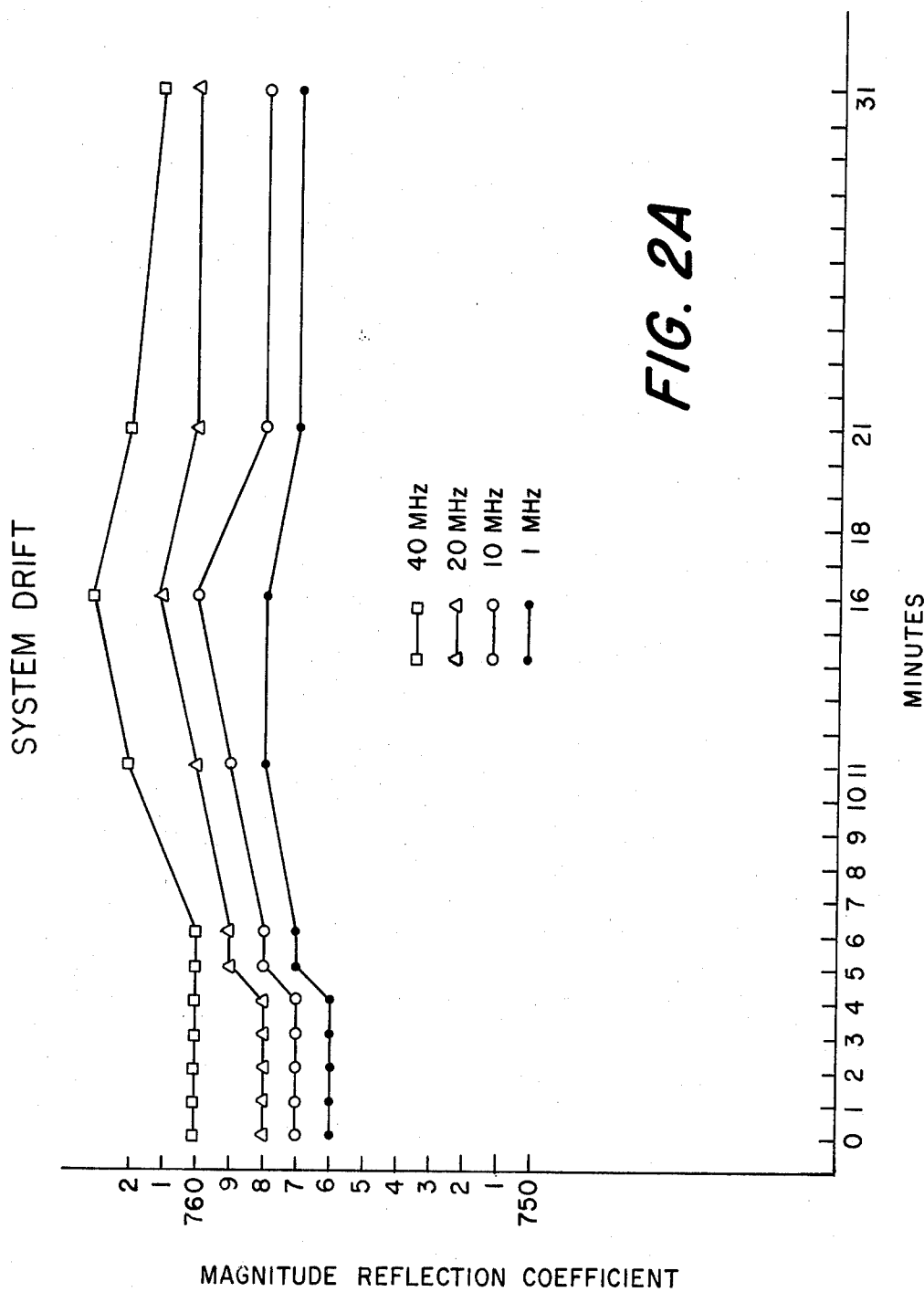

A study of the measurement system's stability is presented in FIGS. 2A and 2B wherefrom it was estimated that phase measurements are accurate to about 0.25° and amplitude measurements are accurate to about 3 parts per throusand. Note that the data are presented for the two extreme frequencies used in the measurements as well as for two intermediate frequencies.

Electrode interface data are demonstrated in Table 1 for the simple and reproducible situation of saline and buffer conductivity at 26° C. with platinum/platinum black bright copper surfaces. An upward trend in these measured values with increasing frequency is apparent. The effect of a polarizable interface is seen to cause a downward bias in the measured values. The MOPS-TRIS buffer also affects the interface and/or conductivity inasmuch as the conductivities are uniformly higher in buffered than in nonbuffered isotonic saline when measured in the platinum chamber.

Figure 3:
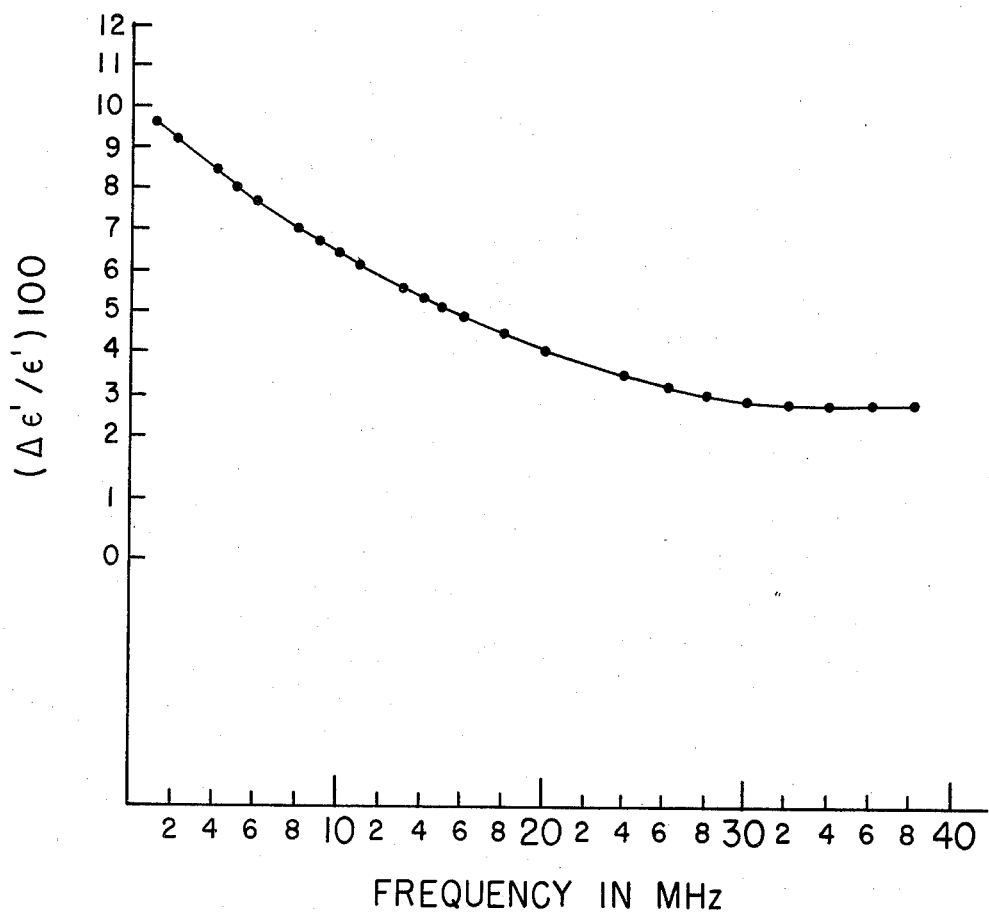
FIGS. 3 and 3A are graphs of the interface effects expressed as a percentage correction factor which is applied to the dielectric constant in FIG. 3A and conductivity, FIG. 3B, obtained with bright copper electrodes to obtain the complex permittivity that would have obtained with platinum/platinum black electrodes.
Figure 3A:
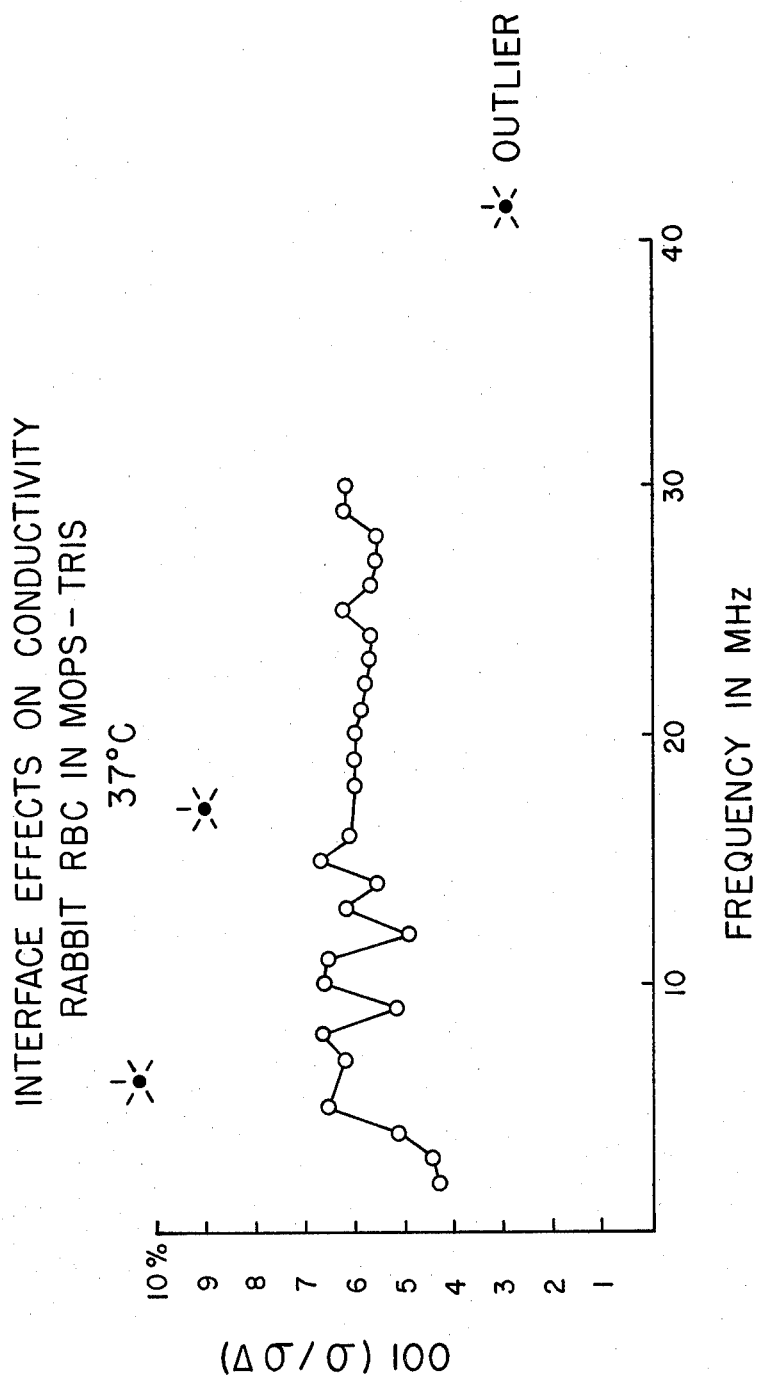

Correction factors which relate to complex permittivity with the platinum black to measured complex permittivity with the bright copper surface are shown in FIGS. 3 and 3A. The use of copper interface results in a downward bias in estimates of both dielectric constant and conductivity when compared to the "nonpolarizable" platinum black interface. Such differences were consistent across species, temperature and suspending media.

TABLE 1

INTERFACE AND SUSPENDING MEDIA EFFECTS ON CONDUCTIVITY

| FREQUENCY IN MHz | SALINE COPPER 26° C. | SALINE, PtB 26° C. | MOPS-TRIS, PtB 26° C. |
|---|---|---|---|
| 1 | 1.36 | 1.67 | 1.59 |
| 2 | 1.49 | 1.68 | 1.76 |
| 3 | 1.55 | 1.73 | 1.82 |
| 4 | 1.55 | 1.73 | 1.81 |
| 5 | 1.57 | 1.75 | 1.83 |
| 6 | 1.55 | 1.73 | 1.81 |
| 7 | 1.56 | 1.75 | 1.83 |
| 8 | 1.54 | 1.72 | 1.80 |
| 9 | 1.55 | 1.74 | 1.81 |
| 10 | 1.55 | 1.74 | 1.82 |
| 11 | 1.55 | 1.74 | 1.82 |
| 12 | 1.55 | 1.74 | 1.82 |
| 13 | 1.54 | 1.73 | 1.82 |
| 14 | 1.55 | 1.75 | 1.83 |
| 15 | 1.56 | 1.75 | 1.84 |
| 16 | 1.56 | 1.75 | 1.84 |
| 17 | 1.56 | 1.76 | 1.84 |
| 18 | 1.56 | 1.76 | 1.84 |
| 19 | 1.57 | 1.76 | 1.85 |
| 20 | 1.56 | 1.75 | 1.85 |
| 21 | 1.56 | 1.76 | 1.84 |
| 22 | 1.56 | 1.75 | 1.84 |
| 23 | 1.56 | 1.76 | 1.84 |
| 24 | 1.56 | 1.75 | 1.84 |
| 25 | 1.57 | 1.77 | 1.86 |
| 26 | 1.57 | 1.76 | 1.84 |
| 27 | 1.57 | 1.77 | 1.86 |
| 28 | 1.58 | 1.77 | 1.87 |
| 29 | 1.58 | 1.77 | 1.86 |
| 30 | 1.57 | 1.78 | 1.85 |
| 31 | 1.56 | 1.76 | 1.85 |
| 32 | 1.57 | 1.77 | 1.85 |
| 33 | 1.57 | 1.78 | 1.85 |
| 34 | 1.56 | 1.77 | 1.85 |
| 35 | 1.58 | 1.78 | 1.86 |
| 36 | 1.57 | 1.77 | 1.85 |
| 37 | 1.57 | 1.79 | 1.87 |
| 38 | 1.57 | 1.78 | 1.87 |
| 39 | 1.58 | 1.79 | 1.87 |
| 40 | 1.58 | 1.79 | 1.88 |

Rabbit blood used for analysis was obtained from Albino and Dutch specimens by cardiac puncture. The blood quantity taken from a single rabbit was between 20 and 30 ccs. The blood was drawn into a heparinized syringe and stored in a refrigerator for periods between 30 minutes and 2 hours before further preparation. Refrigeration was necessary to prevent reduction of energy stores in the cells.

Sheep blood used for analysis was obtained from mixed breed specimens. Approximately 250 ccs. of peripheral blood is collected into an equal volume of Alsever's solution. The blood was stored for periods between 1 and 3 days prior to preparation for the experiment. The blood was centrifuged at 2,000 rpm for 10 minutes in order to remove the cellular components from the serum. The serum and most of the buffing coat were removed by aspiration. The cells were then washed in the final suspending medium with 3 to 5 times volume for three washings. Final suspensions were made with hematocrits between 32 and 35 percent. The blood was returned to the refrigerator for use the next morning.

Canine peritoneal fibroblasts were obtained by peritoneal lavage. The cells were cultured and divided for seven generations (the most generations consistent with eucaryotic states). The cells were harvested with trypsin, then washed 3 times in 5 times volume of isotonic NaCl. Cell viability was assessed with typan blue exclusion. Percentage cell volume was 28%.

The suspending media were all potassium free, and began with isotonic saline and 10 units of heparine (10 μL) per ml. pH experiments were performed in these media plus MOPS-TRIS buffer stabilized for pH of 6.5, 7.0 and 7.5.

Those experiments performed at 37° C. were thermostatically controlled (regulated to 0.1° C.) by water circulated around the chamber containing the specimen. Approximately 0.8 ccs of suspension was used for each experiment.

The pharmacologic agents used were oubain obtained from Calbiochem, valinomycin obtained from Sigma, and gramicidin also obtained from Calbiochem, and collagenase also obtained from Calbiochem. The oubain was prepared by dissolving 5 mg in 5 ml of deionized water. A 100 microliter sample of the stock solution was added to a 700 $\mu$L sample of blood. The final oubain concentration was approximately $10^{-4}$ molar (a value where the activity reaches a maximum). The collagenase was prepared by dissolving 5 mg in 10 cc of isotonic saline.

The oubain was incubated with the rabbit erythrocytes in saline suspension at 37° C. for a period of 75 minutes (oubain is a fast acting cardiac glycoside which reaches 80% of its full effect within 60 minutes). The sample and test set were shaken every 5 minutes throughout the incubation period. Electromagnetic measurements were taken every 15 minutes after every third shaking.

Due to the osmotic shock of a 100 $\mu$L does of oubain stock solution, a control was performed. This consisted of an identical incubation of 100 $\mu$L of deionized water.

An additional control for hemolysis due to the shaking was performed. This consisted of 0.8 cc of cell suspension without any additional reagents taken through the same shaking and measurement regimine.

The valinomycin was prepared by dissolving 5 mg in 10 ml of ethyl alcohol. Reagent activity was verified in a parallel series of erythrocytes by fluorescent measurements according to the methods of Hoffman and Laris, "Determination of Membrane Potentials in Human and Amphiuma Red Blood Cells by Means of A Fluorescent Probe", *J. Physiol.*, 239:519–552, 1974. 10 $\mu$L of this stock solution was added to a sample of blood still in the chamber from the control dispersion analysis. Two minutes of incubation at 37° C. were allowed with shaking just prior to measurement (according to fluorescent measurements, the valinomycin effect is complete within 90 seconds). Final concentration of valinomycin was calculated to be $3 \times 10^{-5}$ molar, but the exact value is uncertain due to the fact that some of the chamber contents was lost when the cap was replaced and the volume topped off with blood. All ionophore experiments were of the before-and-after type in order to minimize variability due to chamber filling. Valinomycin was spectrographically monitored for degradation after several weeks and the stock solution was stored in the dark.

The gramicidin was prepared by dissolving 1 mg in 10 cc of ethyl alcohol. 20 $\mu$L of the stock solution was added to a previously analyzed sample of blood in the same manner as for valinomycin.

Controls for the ethyl alcohol and water solvent were performed. 10 or 20 $\mu$L of the solvent with no additional reagent was introduced and incubated in the same manner as for the ionophores and collagenase.

The ionophoretic activity of the valinomycin and gramicidin was further analyzed by challenging erythrocyte suspensions with and without the ionophore for response to a 30 $\mu$L does of 3 M KCl. The procedure was to measure a blood sample, introduce the ionophore, measure the sample again, then to introduce the KCl followed by the last measurement. The experiment was then repeated with a new blood sample without the step for ionophore addition. In all cases, 2 minutes for incubation and shaking was allowed after any reagent was introduced prior to measurement.

pH measurements were performed in a rapid series following both ascending and descending orders. New blood samples were used for each measurement and replications were employed to define the impact of system instability and interface equilibration. All data presented for pH experiments were done in rapid succession with results tabulated for minimal effect, i.e. opposite to system instability and interface equilibration. Thus, the results presented are diminished by these factors. System instability was diminished with use of a phase locked measurement system. The pH experiments strain the resolution of the instrumentation and stability considerations were much more important for these experiments. Also, pH affects on the electrode interface were examined with the buffer solutions for controls. Control, i.e. buffer, data was collected in the absence of cells.

Cell membrane disruption was accomplished by sonication at 70 watts for 1 minute with 20 KHz sound. A 40% duty cycle was used in order to prevent heating.

The effects due to cell preparation are tabulated in Table 2 for the two extreme circumstances of rabbit erythrocytes in MOPS-TRIS at 37° C. and sheep erythrocytes at 26° C. in saline suspension. Various pair-wise comparisons (expressed as the average-over-frequency for precent change at each frequency) are displayed at Tables 3A, 3B, and 3C for temperature, spaces and media effects. All measurements reported in the Tables were collected with the platinum black surface treatment. Clearly the two types of cell preparation differ substantially in absolute values of permittivity, but the relaxation spectra have very similar shapes.

TABLE 2

RANGE OF PERMITTIVITY CONDITIONS IN ERYTHROCYTE SUSPENSION

| FREQUENCY IN MHz | RABBIT RBC IN MOPS-TRIS at 37° C. | | SHEEP RBC IN SALINE at 26° C. | |
|---|---|---|---|---|
| | $\sigma$ | $\epsilon$ | $\sigma$ | $\epsilon$ |
| 1 | 0.81 | 2471 | 0.83 | 1756 |
| 2 | 1.03 | 1601 | 0.95 | 1062 |
| 3 | 1.19 | 1394 | 1.01 | 788.2 |
| 4 | 1.24 | 1033 | 1.03 | 592.9 |
| 5 | 1.31 | 915.0 | 1.07 | 507.5 |
| 6 | 1.39 | 842.4 | 1.07 | 412.6 |
| 7 | 1.37 | 701.0 | 1.10 | 372.1 |
| 8 | 1.40 | 615.3 | 1.10 | 314.3 |
| 9 | 1.43 | 578.4 | 1.11 | 289.3 |
| 10 | 1.45 | 529.1 | 1.13 | 263.9 |
| 11 | 1.48 | 490.1 | 1.14 | 236.2 |
| 12 | 1.50 | 456.3 | 1.15 | 216.5 |
| 13 | 1.53 | 417.6 | 1.15 | 200.2 |
| 14 | 1.53 | 384.9 | 1.15 | 185.5 |
| 15 | 1.57 | 379.8 | 1.17 | 189.9 |
| 16 | 1.57 | 353.2 | 1.17 | 175.9 |
| 17 | 1.57 | 336.2 | 1.17 | 167.4 |
| 18 | 1.59 | 311.7 | 1.18 | 158.8 |
| 19 | 1.60 | 310.3 | 1.18 | 162.0 |
| 20 | 1.60 | 289.2 | 1.18 | 155.7 |
| 21 | 1.61 | 283.9 | 1.19 | 154.5 |
| 22 | 1.62 | 277.5 | 1.19 | 142.2 |
| 23 | 1.64 | 259.7 | 1.19 | 137.9 |
| 24 | 1.63 | 247.2 | 1.19 | 135.7 |
| 25 | 1.66 | 251.2 | 1.20 | 143.0 |
| 26 | 1.65 | 245.2 | 1.20 | 134.0 |
| 27 | 1.67 | 233.1 | 1.20 | 132.8 |
| 28 | 1.66 | 228.1 | 1.21 | 132.0 |
| 29 | 1.64 | 222.3 | 1.21 | 131.2 |
| 30 | 1.68 | 207.8 | 1.21 | 129.1 |
| 31 | 1.68 | 211.9 | 1.21 | 129.2 |
| 32 | 1.68 | 203.8 | 1.21 | 124.4 |
| 33 | 1.70 | 212.9 | 1.22 | 127.9 |
| 34 | 1.69 | 203.8 | 1.22 | 122.9 |
| 35 | 1.70 | 203.2 | 1.22 | 124.8 |

TABLE 2-continued
RANGE OF PERMITTIVITY CONDITIONS IN ERYTHROCYTE SUSPENSION

| FREQUENCY IN MHz | RABBIT RBC IN MOPS-TRIS at 37° C. | | SHEEP RBC IN SALINE at 26° C. | |
|---|---|---|---|---|
| | $\sigma$ | $\epsilon$ | $\sigma$ | $\epsilon$ |
| 36 | 1.70 | 192.5 | 1.22 | 120.6 |
| 37 | 1.70 | 192.2 | 1.23 | 121.4 |
| 38 | 1.72 | 183.6 | 1.22 | 116.4 |
| 39 | 1.72 | 182.6 | 1.23 | 117.1 |
| 40 | 1.73 | 188.6 | 1.23 | 118.8 |

TABLE 3A
SUSPENDING MEDIA DIFFERENCES WITH RABBIT

| 37° C. | 26° C. |
|---|---|
| Saline is 8.2% lower than MOPS-TRIS | Saline is <1% lower than MOPS-TRIS |

TABLE 3B
TEMPERATURE DIFFERENCES

| Rabbit in MOPS-TRIS | Sheep in Saline |
|---|---|
| 26° C. is 17.6% lower than 37° C. | 26° C. is 19.3% lower than 37° C. |

TABLE 3C
SPECIES DIFFERENCES IN SALINE

| 37° C. | 26° C. |
|---|---|
| Sheep is 24.8% lower than rabbit | Sheep is 26.6% lower than rabbit |

EXAMPLES

The following is a description of the results achieved by utilizing the process of this invention to evaluate cell membrane characteristics.

With reference to the drawings and in particular to FIG. 2, FIG. 2 is a display of the magnitude of the reflection coefficient measured according to the process of this invention as a function of frequency. The reflection coefficient was calculated as described above by measurement of the output of a test capacitor step-wise at 1 MHz intervals between frequencies of 2 and 40 MHz. FIG. 2 also displays a magnitude of the reflection coefficient in an erythrocyte suspension sonicated as described above.

The dispersion due to cell membrane is then visible in the magnitude of the reflection coefficient and, as shown in FIG. 2, this dispersion is markedly reduced in the sonicated sample.

The decrease of dispersion with sonication of the cell suspension is inconsistent with previous studies of osmotically hemolyzed blood. Previous studies state that chemical destruction of the membrane ghosts is necessary before the dispersion is materially changed except at audio frequencies for example 15 KHz. The present experiment differs from those earlier reports in the method of hemolysis. The prior studies used osmotic hemolysis with the addition of as much as seven times the volume of distilled water. As a result, the conductivities are substantially decreased and the ionic concentrations are markedly diluted. In addition, there are grounds to question the degree of membrane fragmentation with osmotic hemolysis. Since the agent is hydrostatic force, a single tear in a cell membrane would be sufficient to release hemoglobin, but the ghosts or vesicles may reseal into smaller effective volumes which commence to concentrate potassium and extrude sodium. The greater membrane fragmentation with sonication would effectively diminish any such volume containment. Also, it is important to measure the dispersion immediately after sonication since vehicles seem to form within three or four hours after sonication.

Figure 4:
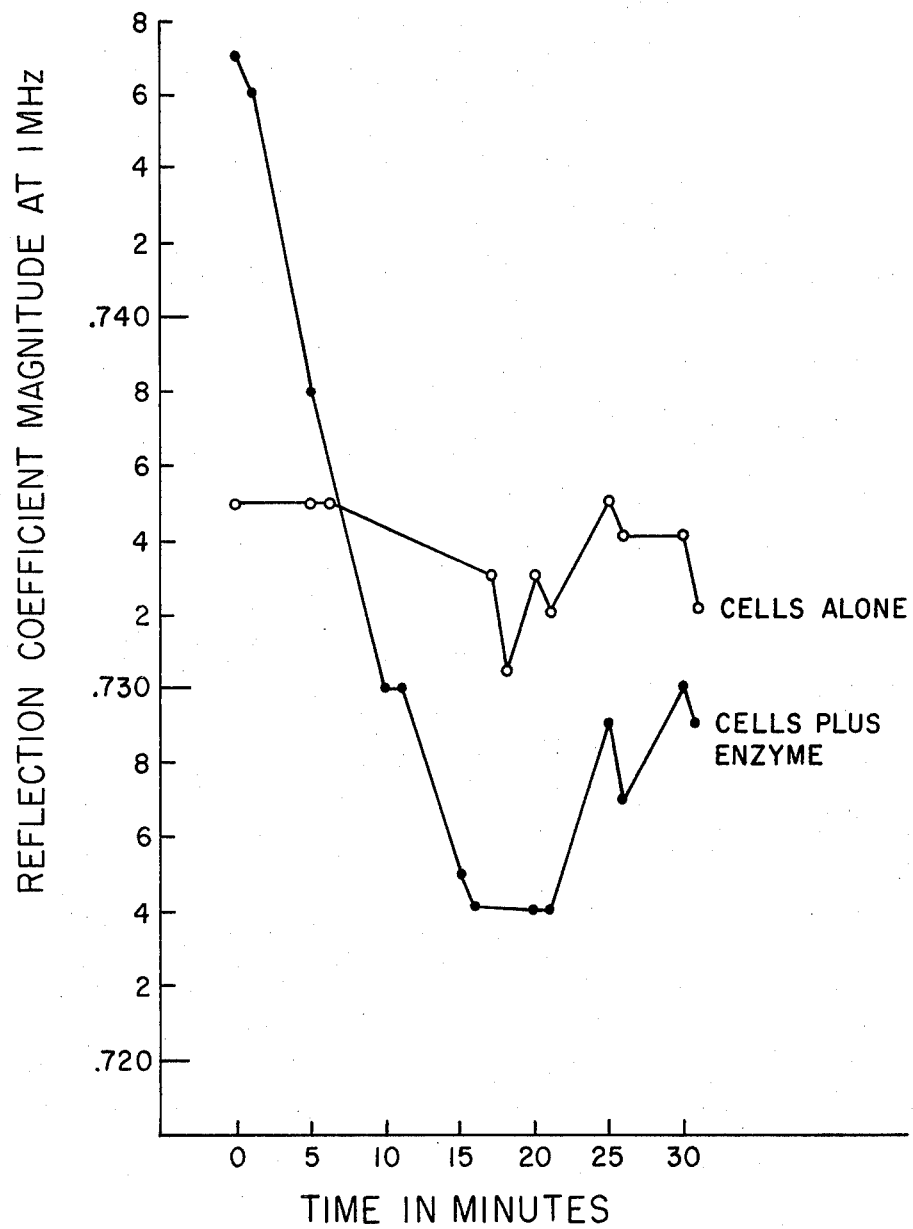
FIG. 4 is a graph of the magnitude of the complex reflection coefficient for a saline suspension of cultured canine peritoneal (28% cell volume fraction) displayed as a function of time since the origin with and without incubation with collagenase.

The canine peritoneal fibroblasts in saline suspension are shown in FIG. 4 wherein control and collagenase treated cells are compared by the time course of change in the magnitude of the complex reflection coefficient ($\rho$) at 1 MHz. The time origin corresponds to introduction of the cells into the chamber. It is notable that at all frequencies the treated and untreated cells differed in the time course of $\rho$, but the greatest differences were observed at 1 MHz. At the end of the time course, approximately 10% of the treated cells no longer excluded dye. In the untreated group, approximately 1% failed to exclude dye.

Figure 5:
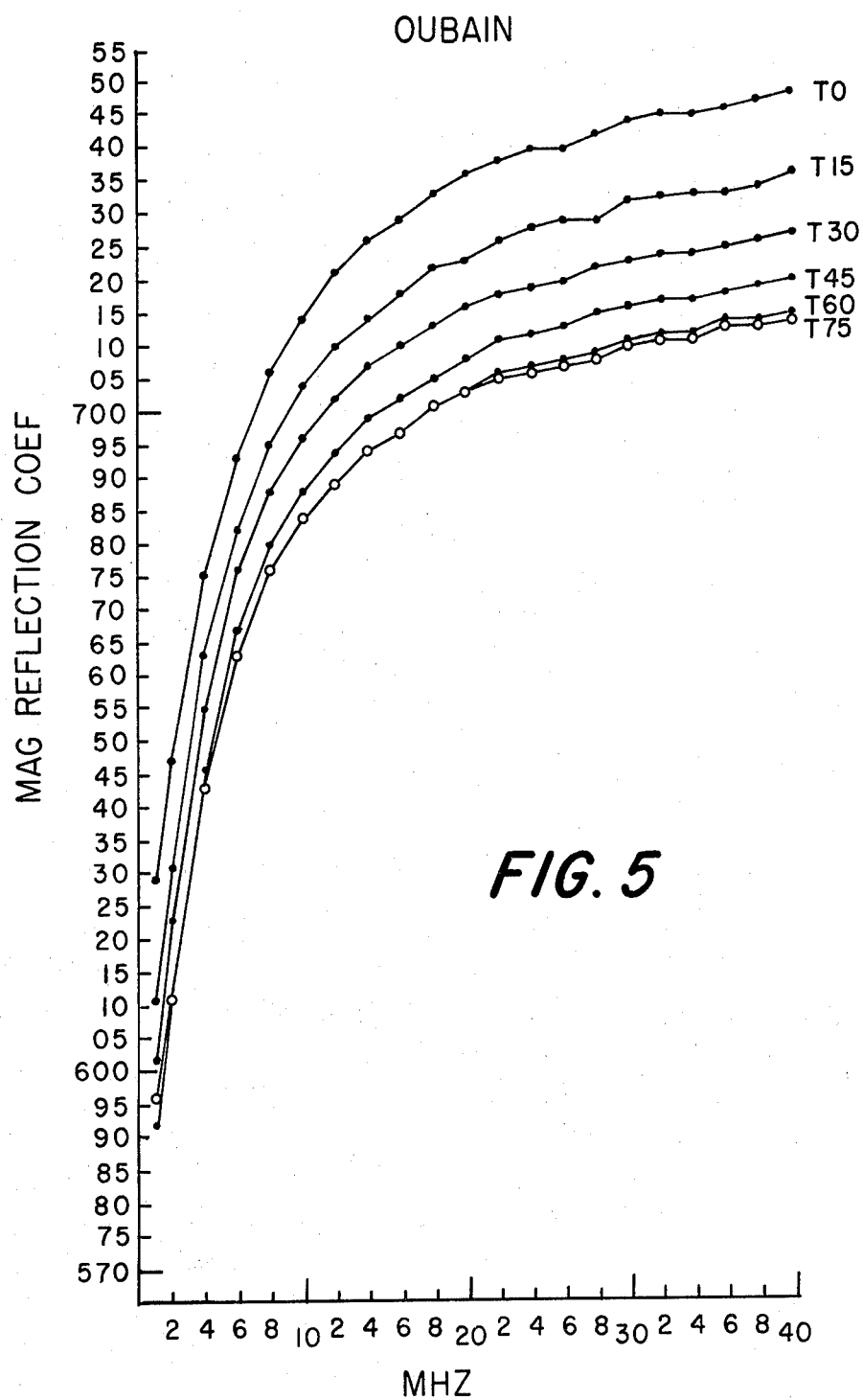
Figure 5A:
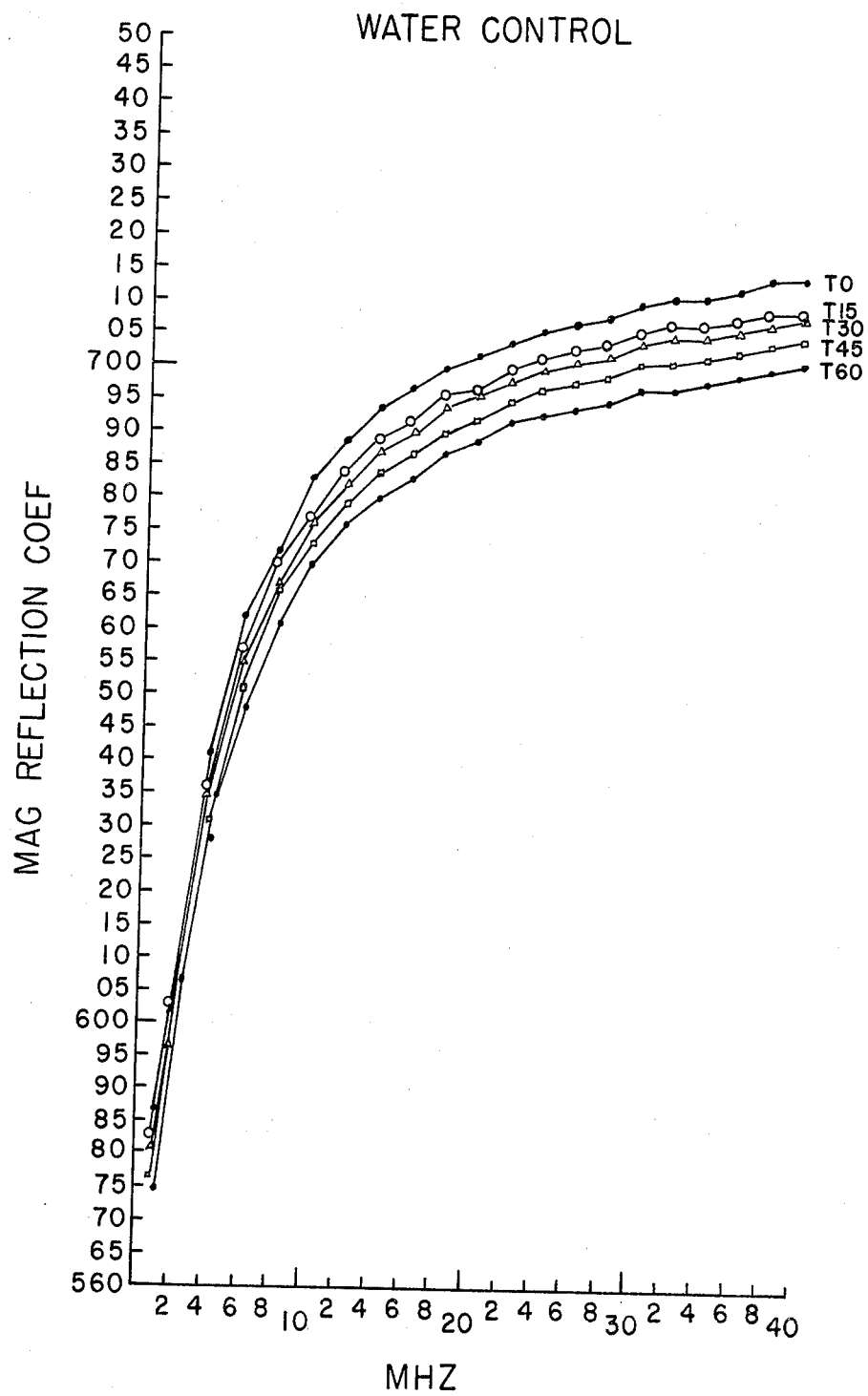
Figure 6:
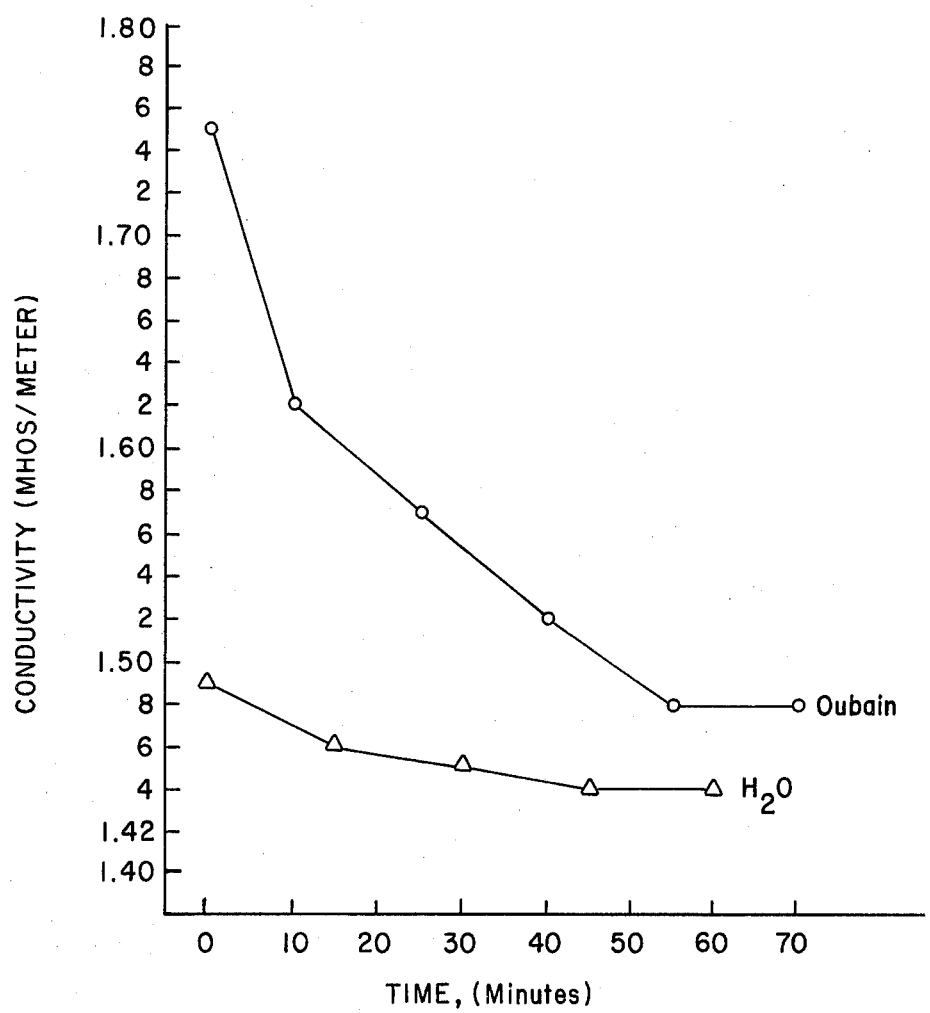
FIGS. 6, 6A and 6B are graphs of the time course of conductivity at 40 MHz in FIG. 6 and 10 MHz in FIG. 6A displayed for oubain and water incubated rabbit erythrocytes; the time course of conductivity for the shaker control at 40 and 10 MHz is displayed in FIG. 6B.
Figure 6A:
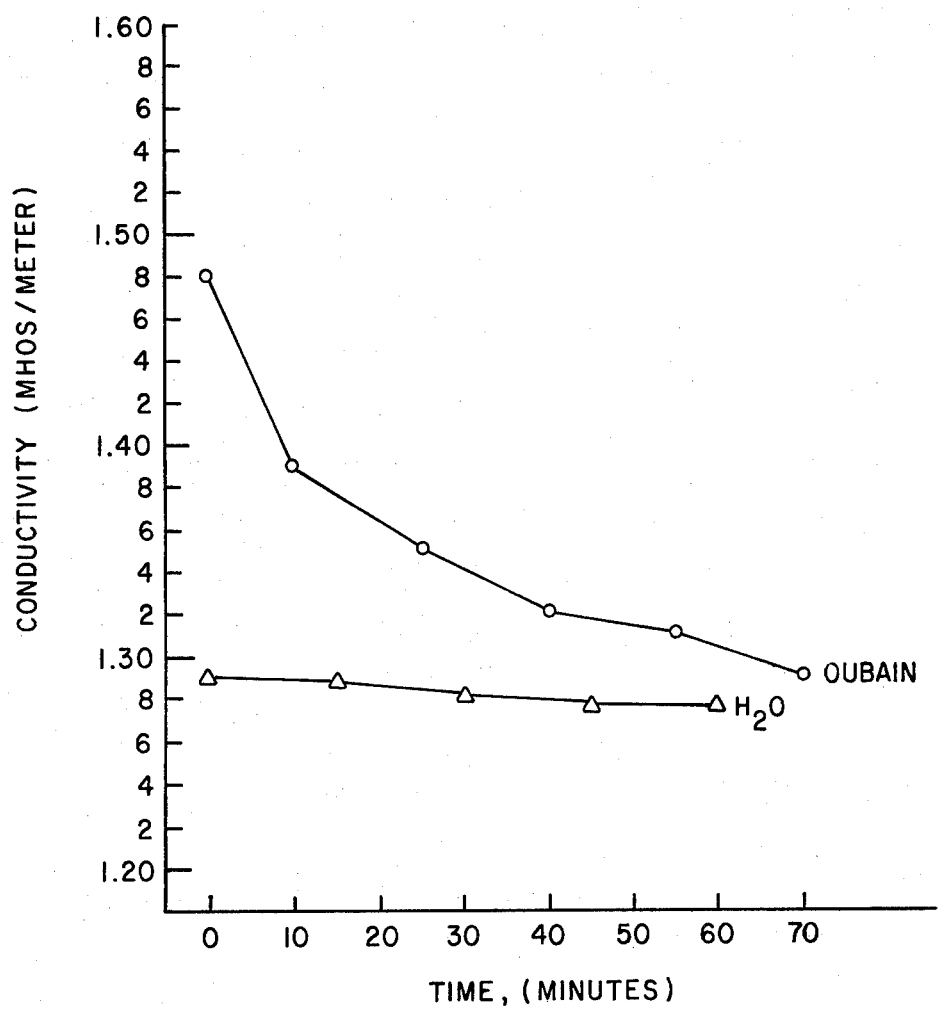
Figure 6B:
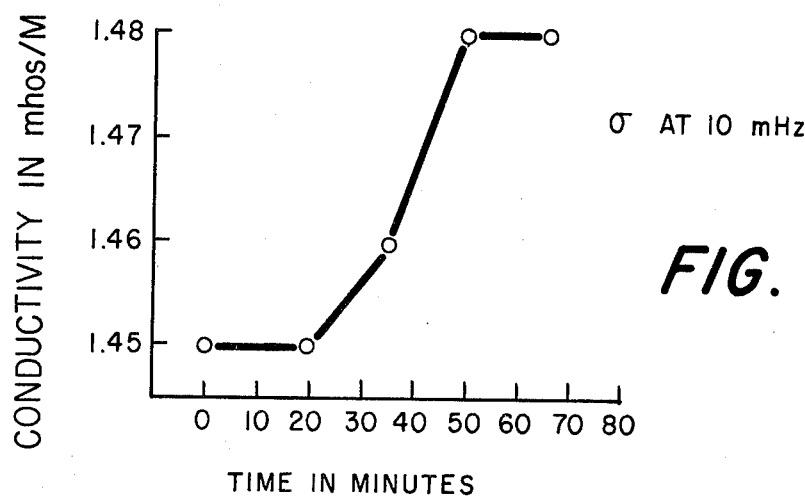
Figure 6C:
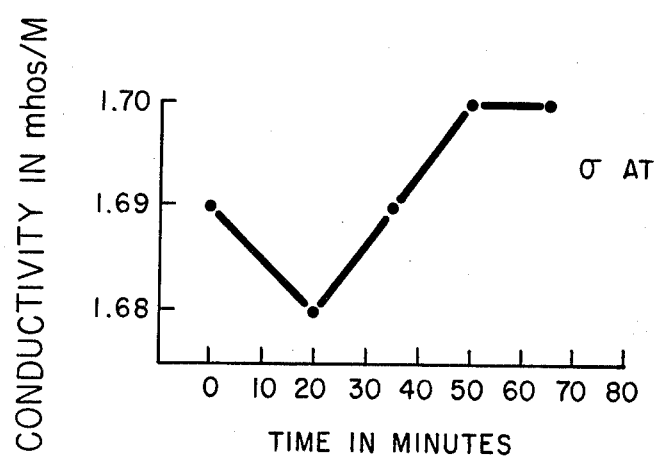

The results of the oubain experiment are shown in FIGS. 5, 5A and 5B for the complex reflection coefficient magnitude and in FIGS. 6, 6A and 6B for conductivity at the two selected frequencies of 10 MHz and 40 MHz. FIG. 5 represents the time course of changes in the dispersion of $\rho$ for a saline suspension of rabbit erythrocytes during incubation with oubain. FIG. 5A represents $\rho$ as a function of time for the osmotic control, whereas 5B presents $\rho$ as a function of time with only periodic shaking of the chamber. Likewise, FIG. 6 is the time course of changes in conductivity with oubain incubation; FIG. 6A is the time course with water incubation; and FIG. 6B is the time course for cell shaking. Conductivity values are presented at the same location in time as for the reflection coefficient data, but only two frequencies are displayed because the greatest differences between treated and control samples were at high frequencies with effects substantially decreasing below 10 MHz. Either set of data indicates that the osmotic control moves the permittivity in the same direction as oubain treatment, and that the effect of shaking is in the opposite direction. However, the water and oubain treatments differ in their time course and final values.

Figure 7:
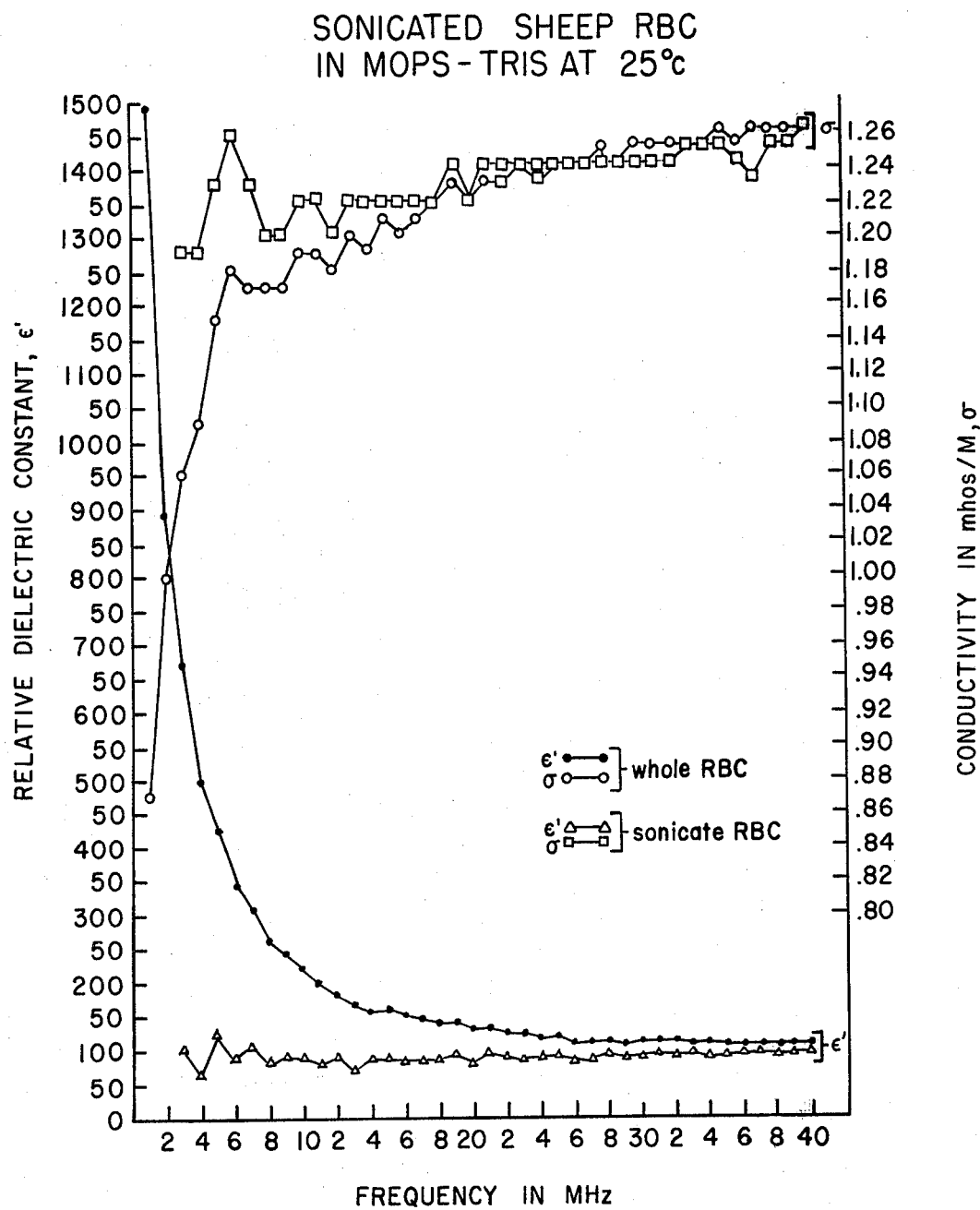
FIG. 7 is a graph of the effect of cell disruption by sonication on the dispersion of complex permittivity displayed for a MOPS-TRIS buffered (pH 7.0) suspension of sheep erythrocytes (Hct 35%)

The data in FIG. 7 demonstates a classical dielectric relaxation in the dispersion of complex permittivity for a buffered suspension of intact sheep erythrocytes. This is manifest by decreasing dielectric constant and increasing conductivity as the interrogating frequency is increased from 1 MHz to 40 MHz. The sonicated sample is markedly different with relatively frequency independent values of dielectric constant and conductivity. At the lower frequency, the sonicated and intact cells depart most markedly. The intact cell suspension demonstrates progressively lower conductivity and progressively higher dielectric constant in comparison to the sonicated cells as the interrogating frequency approaches 1 MHz. At the upper limiting frequency of 40 MHz the two treatments have differences in conductivity and dielectric constant which are minimal. Dispersion of permittivity in the sonicated cells, while greatly diminished in comparison to the intact cell suspension, is not reduced to that observed with the buffered saline alone. Neither do the conductivity values of the sonicated sample approach that of the buffer.

Figure 8:
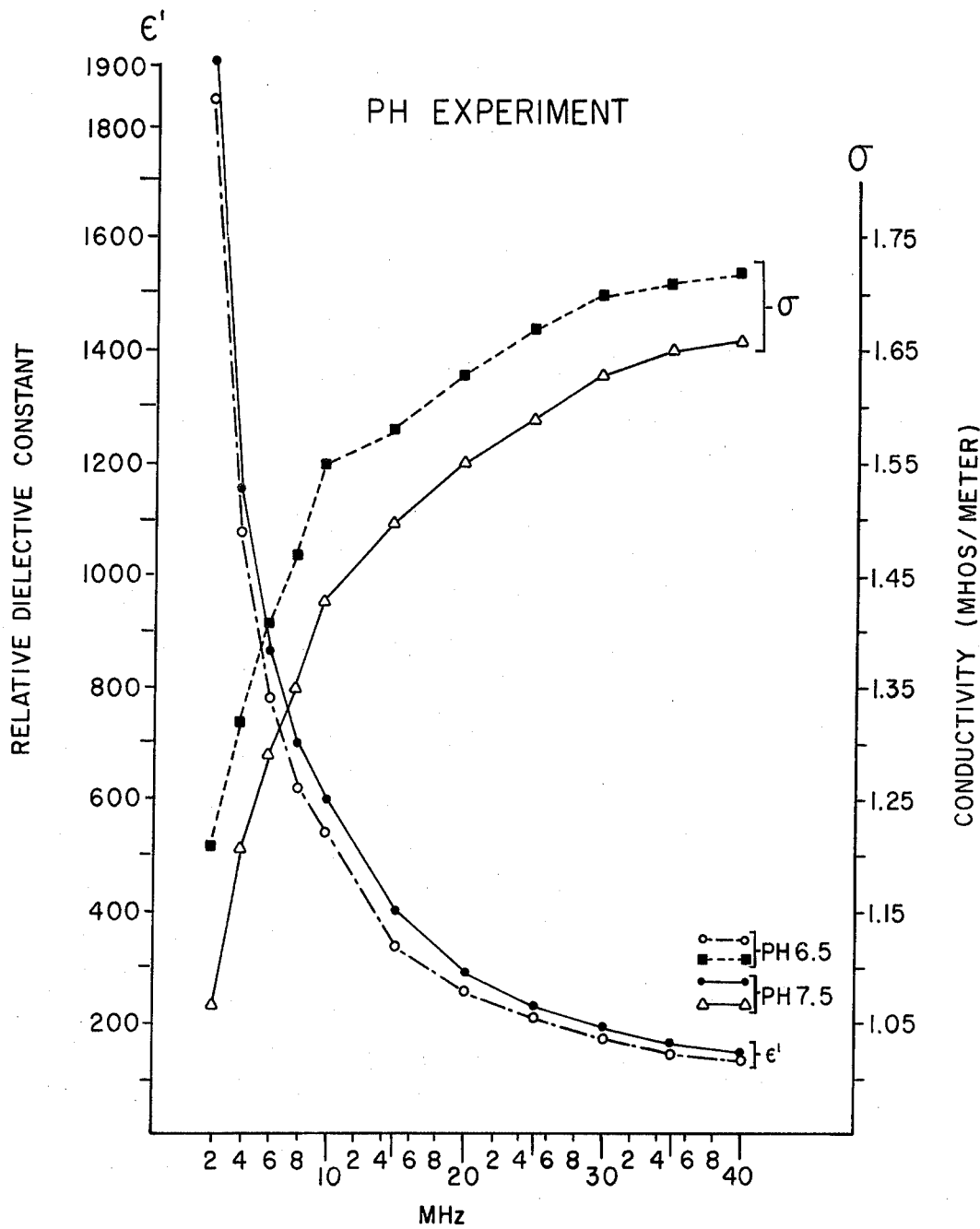
FIG. 8 is a graph of the effect of pH on the complex permittivity displayed for a rabbit erythrocyte suspension (34% Hct) in isotonic saline buffered with a MOPS-TRIS at pH 6.5 and pH 7.5.

The results of the pH experiments are shown in FIG. 8. The three pHs are distinguishable in that increasing the pH from 6.5 to 7.5 decreases conductivity at all frequencies with the greatest effect at 1 MHz. Conversely, higher pH increases dielectric constant, again with the greatest effect at low frequency. The results with pH 7.0 are intermediate between those of pH 6.5 and 7.5. pH does alter the interface, but the direction of its effect is opposite in the buffer series alone than in the buffered cell suspensions.

Figure 9:
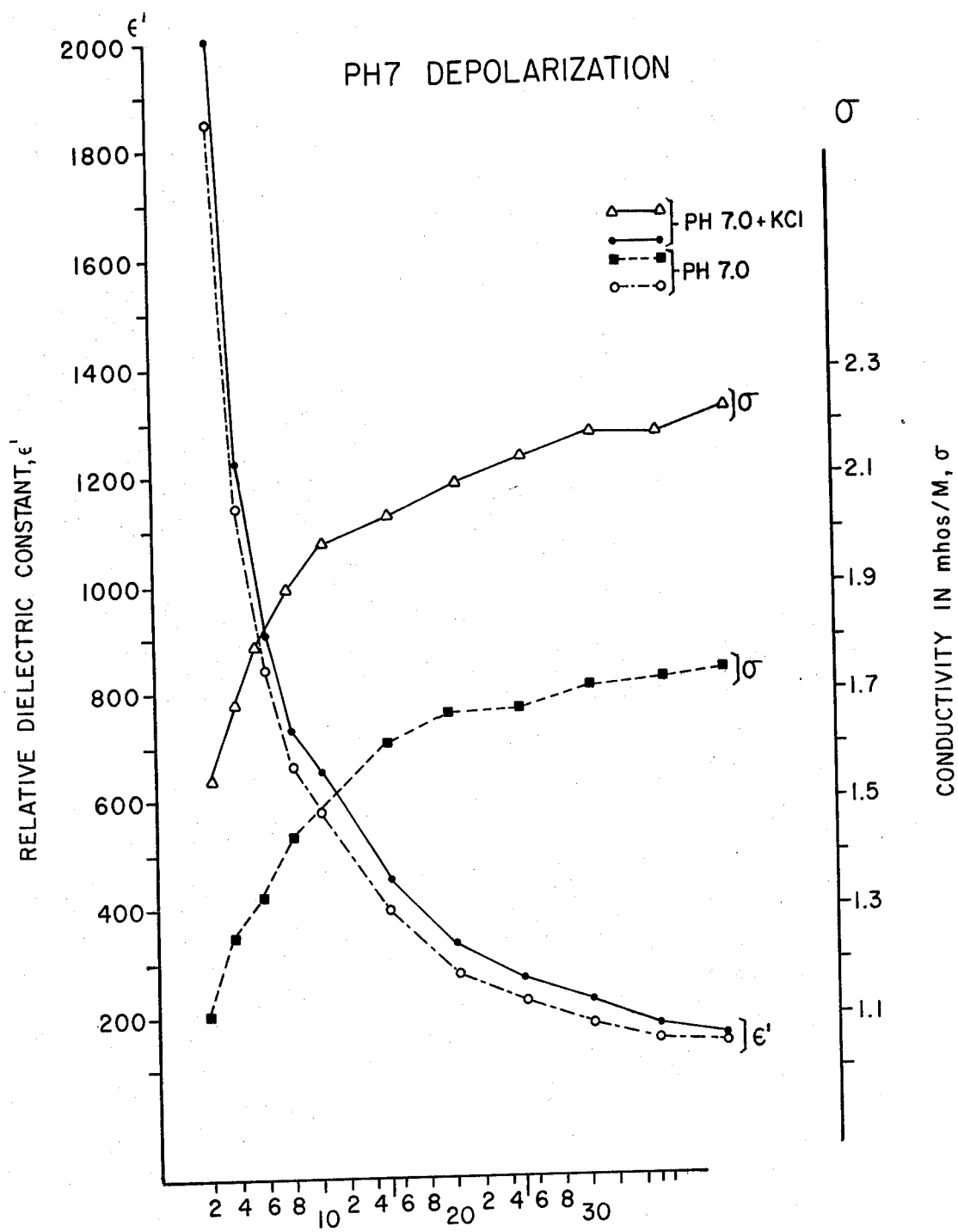
FIG. 9 is a graph of a MOPS-TRIS buffered rabbit erythrocyte suspension depolarized with extracellular KCl expressed as an effect on the dispersion of complex permittivity.

Depolarization of the erythrocyte suspension with extracellular KCl has a marked effect on the dispersion of complex permittivity as shown in FIG. 9. The action on conductivity is, of course, to greatly elevate the values at all frequencies. There is also a small upward shift in the dielectric constant at all frequencies, and a change in dispersion which is to be presented in the following paragraphs.

The results of the ionophore experiments are presented in FIGS. 10 and 11A, 11B, 11C and 11D. The ionophore alone has little effect except at the lowest frequencies. The direction of this effect is to increase conductivity differentially at the frequencies thereby decreasing dispersion as shown in FIG. 10. In addition, FIG. 10 illustrates that most of the effect due to the ethyl alcohol solvent alone is on conductivity unlike the effect of an equal volume (10 microliter) of water solvent which increases the dielectric constant rather than the conductivity. There is little evidence to suggest that gramicidin is different than valinomycin in that the direction and magnitude of its effect is similar to valinomycin.

When the cell suspension is challenged with an extracellular KCl does before and after treatment with ionophore, it is apparent that the control and treatment groups respond differently. Specifically, FIGS. 11 and 11A illustrate that the KCl challenge increased the dispersion in conductivity in the untreated erythrocytes. On the other hand, pretreatment with valinomycin in one case reserved the effect; and in the other case, greatly diminished the effect. In other words, pretreatment with ionophore diminished or prevented the increase in conductivity dispersion produced with extracellular KCl challenge.

Because conductivity is markedly temperature sensitive, difficulties exist when the imaginary part of the complex relative permittivity greatly exceeds the real part. With the system described herein, the method must be limited to samples wherein the imaginary part and real part are within two orders of magnitude. This is no problem with biological samples containing cells, but the analysis of electrolytes with concentrations above $2 \times 10^{-3}$ M in the absence of cells must be limited to conductivity since the dielectric constant is not readily obtainable. Note, for example, that the estimated dielectric constant in the hemolyzed red blood cell sample of FIG. 7 is close to the expected value of 78 with little dispersion; however, the values are consistently about 10% high. Accuracy in the lower frequency range decreases for frequencies below 4 or 5 MHz, with greatest errors at 1 MHz.

The error introduced by polarizable electrodes (see FIG. 3) is in the order of 6% for conductivity and a maximum of 10% for dielectric constant at the lower limiting frequency of 1 MHz. The effect of a polarizable electrode-electrolyte interface is to insert a polarization impedance in series with the sample impedance. As a result, the effect is reproducible for a given set of ionic conditions and suitable for a frequency dependent correction factor. The reason for correction rather than use of the platinum black surface treatment throughout was the difficulty in obtaining reproducible platinum/platinum black coatings, the short time such coating remained stable and most importantly the very lengthy equilibration times required for this surface. Furthermore, the platinum/platinum black system is markedly pH dependent.

A most significant additional limitation is the consequence of the range of operating frequencies. In the present case, the low frequency limit is determined by inaccuracies and irreproducibility in the HP 8507 network analyzer when working in the lower frequency range of 500 KHz to 4 or 5 MHz. These problems are compounded by the very high dielectric constant of blood at these frequencies. In addition, electrode polarization becomes more significant as the frequency is reduced below 1 MHz, even with platinum/platinum black surface treatment. The combination of these features for measurements in the HF band indicates that high speed, automatic network analysis methods must be adapted to four terminal designs. Likewise, a different network analyzer will be required to operated at frequencies significantly below 1 MHz. In the HF band, however, the instrument inaccuracies in phase measurement below 4 MHz greatly exceed the effects due to interfaces. The accuracy of the phase measurements further deteriorates as the phase angle approaches 180° at low frequencies. As noted above at high frequencies, the present system is confined to frequencies below 200 MHz.

Concerning results of the experiments, the decrease of dispersion with sonication of the cell suspension as shown in FIG. 7 is inconsistent with previous studies of osmotically hemolyzed blood. Previous studies state that chemical destruction of the membrane ghosts is necessary before the dispersion is materially changed except at audio frequencies. The present experiment differs from the earlier reports in the method of hemolysis.

The incomplete loss of dispersion for sonicated cells in comparison with the buffer and failure of convergence of conductive values in the sonicated sample and buffer may well represent the resistivity of the cell membrane fragments or vesicles which still exist in the sonicated sample. The conductivity as a function of frequency demonstrates a small consistant upward trend with frequency.

The case with intact cells represents lower conductivity at low frequencies because the reactance of the cell membrane prevents current induction in the intracellular space. The cells, therefore, represent regions of lower conductivity which are in a sense volume averaged with the region of high conductivity (the extracellular space) to reduce the "bulk" conductivity at low frequencies. As the frequency of analysis is increased, the cell membrane reactance is progressively diminished and the "bulk" conductivity approaches that of the hemolyzed sample. Similarly, the dielectric constant of the sonicated sample is only that due to the $H_2O$ solvent. The very large values of dielectric constant with intact cells is completely abolished with the sonicated sample. The interpretation of this finding depends upon the interface between extracellular and intracellular spaces. This interfaces is, of course, destroyed with sonication. In other words, the heterogeneous dielectric of intact cells in suspension is converted to a homogeneous dielectric by sonication.

With reference to FIG. 4, collangenase produces hydrolytic cleavage of the collagen molecule. Collagen is a prominent component of fibroblasts. As a result, collangenase effects cell surface charge states and membrane structure. Predictably, these actions are most apparent at 1 MHz as shown in FIG. 4. The early large differences may reflect this effect.

Oubain blocks the activity of the membrane transport mechanisms responsible for concentrating potassium ion in and extruding sodium ion from the intracellular space. The effect of this agent is to hyperpolarize the cell membrane by a movement of transmembrane potential from chloride equilibrium toward a more negative value. This is the result of passive diffusion of cations along their concentration gradients. Potassium ion moves outward and sodium ion moves inward. The effective permeability increase of sodium ion exceeds that of potassium ion since sodium ion is enhanced by transmembrane potential whereas potassium ion movement is retarded by the same mechanism. The result is that water enters the cell. This is a plausible explanation of why water movement alone acts in the same direction as oubain as shown in FIGS. 5 and 6.

The ionophore results (FIG. 10) demonstrate the effect of increased cation conductance. In the case of valinomycin, the effect is specific for potassium ion. Gramicidin increases conductivity for all cations (sodium ion, potassium ion and hydrogen ion). A comparison of the change in dispersion from the control situation with a KCl dose in the presence and absence of valinomycin shows that KCl alone increases the dispersion more then KCl with valinomycin as seen in FIG. 11. It is believed that KCl alone effects the extracellular space to a larger extent than KCl plus valinomycin since the ionophore will allow more of the extracellular dose to reach the intracellular space. Similar arguments apply to the gramicidin results, but sodium ion and hydrogen ion movements complicate the interpretation. In general, the interpretation of the ionophore and depolarization experiments of FIGS. 9–11 is made more difficult due to the fact that changes in cell volume cannot be separated from changes in transmembrane potential. Ion specific electrodes would be necessary in order to further distinguish the possibility since interpretation becomes more difficult when multiple ion species are involved.

Alcohol alone, as shown in FIG. 10, appeared to produce effects similar to the ionophore dose. Temperature effects also complicate the situation. This is why a KCl challenge is necessary to affirm the permeability alterations. The ionophore alone does decrease dispersion by increasing conductivity in the extra-cellular space.

With reference to the pH experiments, FIG. 8, as the pH is shifted toward 6.5, the charge on the hemoglobin becomes more negative and the transmembrane potential moves toward depolarization. Conversely, as the pH moves toward 7.5, the charge in the hemoglobin becomes less negative and the transmembrane potential moves toward hyperpolarization. The lengthy equilibrium period and pH stabilized washing presumably buffers the intracellular pH to the same value as the extracellular pH, but no direct confirmation of this condition could be performed.

In summary, then, a method for the high speed, noninvasive, electromagnetic analysis of cell suspension physiology and induced pathophysiology has been presented. The method is especially suitable for pathophysiological applications where a high rate of data acquisition is necessary. This requirement is met by the technique of automatic network analysis and offline processing to derive complex permittivity from the error corrected complex reflection coefficient.

The present system offers some freedom from interfacial effects that plague all permittivity measurements in electrolytes insofar as platinum/platnum black is used only in a calibration step. Due to the limitations and the absolute accuracy of phase measurement, and interface equilibration, overall system accuracy is acceptable only under specific conditions. These conditions exclude measurements above 200 MHz, below 1 MHz, and require that the ratio of the imaginary part of the complex permittivity divided by the real part of the complex permittivity be within 0.01 and 100.

The method of this invention offers the potential for noninvasive measurement whereby the contribution of the intracellular and extracellular spaces may be separately analyzed. It was asserted that the physiological foundation for the observed dispersion is the cell membrane and that its activity may be inferred without the need for membrane disruption.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced herein.

What is claimed and desired to be secured by United States Letters Patent is:

1. A method for noninvasive analysis of cell membrane physiology and pharmacology by measurement of the reflection coefficient with electromagnetic energy in the high frequency band applied to cellular suspensions in order to evaluate the selective permeability thereof comprising the steps of subjecting a sample of cell suspension to two port automatic network analysis step-wise over a plurality of preselected frequencies in the high frequency band and measuring the reflection coefficient thereof for each of the plurality of preselected frequencies and calculating the complex permittivity at each of the plurality of preselected frequencies to determine contrast between the introcellular and extracellular spaces based upon the dispersion of complex permittivity.

2. The method of claim 1 which employs a capacitive termination of a test set for a first of said ports for said analysis; and measuring the complex reflection coefficient of said cell suspension in said capacitive termination in response to a plurality of known frequency inputs not to exceed a range of 100 MHz to 500 MHz.

3. The method of claim 2 wherein said analysis is carried out at 1 MHz steps throughout the range of from 1 to 40 MHz.

4. The method of claim 3 further comprising providing a capacitive termination for said analysis consisting of a coaxial chamber fabricated from a female type N bulkhead connector having a center conductor and a shell therearound wherein said cell suspension is disposed between the outer surface of the center conductor and the inner surface of the surrounding shell, and correcting said measured coefficient for the polarization impedance attributable to said conductors.

5. The method of claim 4 wherein said sample is a cell suspension selected from the group consisting of red blood cells and fibroblasts.

6. The method of claim 4 wherein said sample is suspended in a physiological medium.

* * * * *